United States Patent
Willmitzer et al.

(10) Patent No.: US 6,570,066 B1
(45) Date of Patent: May 27, 2003

(54) NUCLEOTIDE SEQUENCES ENCODING ENZYMES THAT ALTER THE CARBOHYDRATE CONCENTRATION AND COMPOSITION IN PLANTS

(75) Inventors: Lothar Willmitzer, Berlin (DE); Christoph Kröger, Hamburg (DE); Stephanie Lütticke, Hamburg (DE); Horst Lörz, Hamburg (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/609,040

(22) Filed: Jun. 30, 2000

Related U.S. Application Data

(63) Continuation of application No. 08/726,705, filed on Oct. 7, 1996, now abandoned, which is a continuation-in-part of application No. 08/104,158, filed on Aug. 13, 1993, now Pat. No. 6,215,042.

(30) Foreign Application Priority Data

Feb. 13, 1991 (DE) .......................................... 41 04 782

(51) Int. Cl.$^7$ ............................ A01H 5/00; C12N 15/82; C12N 5/04

(52) U.S. Cl. ........................ 800/284; 800/298; 800/312; 800/317; 800/320; 536/23.2; 536/23.6; 435/419; 435/252.3

(58) Field of Search ............................ 536/23.6, 23.2; 800/298, 284, 312, 320, 317; 435/69.1, 320.1, 419, 468, 252.3

(56) References Cited

PUBLICATIONS

Chibbar et al. (1995) "Starch Modification in wheat by Genetic Engineering: Problems and Prospects" in, Value added Cereals Through Biotechnology, Saskatoon, Jun. 10–13, p. 21.

Nair et al. (1995) "Cloning, Characterization and Expression Analysis of Branching Enzyme Genes in wheat" in, Value Added Cereals Through Biotechnology, Saskatoon, Jun. 10–13, p. 68.

*Primary Examiner*—Elizabeth F. McElwain
(74) *Attorney, Agent, or Firm*—Frommer Lawrence & Haug LLP

(57) ABSTRACT

Nucleotide sequences encoding enzymes that alter the carbohydrate concentration and composition in plants are described. The sequences encode branching enzymes which alter the amylose/amylopectin ratio in the starch of plants.

26 Claims, 5 Drawing Sheets

(1 of 5 Drawing Sheet(s) Filed in Color)

Plasmid p33-BE 14,6 kb

Plasmid p33 - anti- BE 14,6 kb

SEQUENCE LISTING

<160> NUMBER OF SEQ ID NOS: 4

<210> SEQ ID NO 1
<211> LENGTH: 2909
<212> TYPE: DNA
<213> ORGANISM: Solanum tuberosum
<220> FEATURE:
<221> NAME/KEY: CDS
<222> LOCATION: (2)..(1699)
<223> OTHER INFORMATION: BRANCHING ENZYME

<400> SEQUENCE: 1 t cag gag cgg tct tgg gat att tct tcc acc cca aaa tca aga gtt aga    49
  Gln Glu Arg Ser Trp Asp Ile Ser Ser Thr Pro Lys Ser Arg Val Arg

```
                -continued 1               5              10              15
aaa gat gaa agg atg aag cac agt tca gct att tcc gct gtt ttg acc      97
Lys Asp Glu Arg Met Lys His Ser Ser Ala Ile Ser Ala Val Leu Thr
                20              25              30 gat gac aat tcg aca atg gca ccc cta gag gaa gat gtc aac act gaa     145
Asp Asp Asn Ser Thr Met Ala Pro Leu Glu Glu Asp Val Asn Thr Glu
        35              40              45 aat att ggc ctc cta aat ttg gat cca act ttg gaa cct tat cta gat     193
Asn Ile Gly Leu Leu Asn Leu Asp Pro Thr Leu Glu Pro Tyr Leu Asp
 50              55              60 cac ttc aga cac aga atg aag aga tat gtg gat cag aaa atg ctc att     241
His Phe Arg His Arg Met Lys Arg Tyr Val Asp Gln Lys Met Leu Ile
65              70              75              80 gaa aaa tat gag gga ccc ctt gag gaa ttt gct caa ggt tat tta aaa     289
Glu Lys Tyr Glu Gly Pro Leu Glu Glu Phe Ala Gln Gly Tyr Leu Lys
                85              90              95 ttt gga ttc aac agg gaa gat ggt tgc ata gtc tat cgt gaa tgg gct     337
Phe Gly Phe Asn Arg Glu Asp Gly Cys Ile Val Tyr Arg Glu Trp Ala
        100             105             110 cct gct gct cag gaa gca gaa gtt att ggc gat ttc aat ggt agg aac     385
Pro Ala Ala Gln Glu Ala Glu Val Ile Gly Asp Phe Asn Gly Arg Asn
        115             120             125 ggt tct aac cac atg atg gag aag gac cag ttt ggt gtt tgg agt att     433
Gly Ser Asn His Met Met Glu Lys Asp Gln Phe Gly Val Trp Ser Ile
130             135             140 aga att cct gat gtt gac agt aag cca gtc att cca cac aac tcc aga     481
Arg Ile Pro Asp Val Asp Ser Lys Pro Val Ile Pro His Asn Ser Arg
145             150             155             160 gtt aag ttt cgt ttc aaa cat ggt aat gga gtg tgg gta gat cgt atc     529
Val Lys Phe Arg Phe Lys His Gly Asn Gly Val Trp Val Asp Arg Ile
                165             170             175 cct gct tgg ata aag tat gcc act gca gac gcc aca aag ttt gca gca     577
Pro Ala Trp Ile Lys Tyr Ala Thr Ala Asp Ala Thr Lys Phe Ala Ala
        180             185             190 cca tat gat ggt gtc tac tgg gac cca cca cct tca gaa agg tac cac     625
Pro Tyr Asp Gly Val Tyr Trp Asp Pro Pro Pro Ser Glu Arg Tyr His
        195             200             205 ttc aaa tac cct cgc cct ccc aaa ccc cga gcc cca cga atc tac gaa     673
Phe Lys Tyr Pro Arg Pro Pro Lys Pro Arg Ala Pro Arg Ile Tyr Glu
        210             215             220 gca cat gtc ggc atg agc agc tct gag cca cgt gta aat tcg tat cgt     721
Ala His Val Gly Met Ser Ser Ser Glu Pro Arg Val Asn Ser Tyr Arg
225             230             235             240 gag ttt gca gat gat gtt tta cct cgg att aag gca aat aac tat aat     769
Glu Phe Ala Asp Asp Val Leu Pro Arg Ile Lys Ala Asn Asn Tyr Asn
                245             250             255 act gtc cag ttg atg gcc ata atg gaa cat tct tac tat gga tca ttt     817
Thr Val Gln Leu Met Ala Ile Met Glu His Ser Tyr Tyr Gly Ser Phe
        260             265             270 gga tat cat gtt aca aac ttt ttt gct gtg agc aat aga tat gga aac     865
Gly Tyr His Val Thr Asn Phe Phe Ala Val Ser Asn Arg Tyr Gly Asn
        275             280             285 ccg gag gac cta aag tat ctg ata gat aaa gca cat agc ttg ggt tta     913
Pro Glu Asp Leu Lys Tyr Leu Ile Asp Lys Ala His Ser Leu Gly Leu
        290             295             300 cag gtt ctg gtg gat gta gtt cac agt cat gca agc aat aat gtc act     961
Gln Val Leu Val Asp Val Val His Ser His Ala Ser Asn Asn Val Thr
305             310             315             320 gat ggc ctc aat ggc ttt gat att ggc caa ggt tct caa gaa tcc tac    1009
```

```
                                                                -continued

Asp Gly Leu Asn Gly Phe Asp Ile Gly Gln Gly Ser Gln Glu Ser Tyr
                325                 330                 335 ttt cat gct gga gag cga ggg tac cat aag ttg tgg gat agc agg ctg     1057
Phe His Ala Gly Glu Arg Gly Tyr His Lys Leu Trp Asp Ser Arg Leu
            340                 345                 350 ttc aac tat gcc aat tgg gag gtt ctt cgt ttc ctt ctt tcc aac ttg     1105
Phe Asn Tyr Ala Asn Trp Glu Val Leu Arg Phe Leu Leu Ser Asn Leu
        355                 360                 365 agg tgg tgg cta gaa gag tat aac ttt gac gga ttt cga ttt gat gga     1153
Arg Trp Trp Leu Glu Glu Tyr Asn Phe Asp Gly Phe Arg Phe Asp Gly
    370                 375                 380 ata act tct atg ctg tat gtt cat cat gga atc aat atg gga ttt aca     1201
Ile Thr Ser Met Leu Tyr Val His His Gly Ile Asn Met Gly Phe Thr
385                 390                 395                 400 gga aac tat aat gag tat ttc agc gag gct aca gat gtt gat gct gtg     1249
Gly Asn Tyr Asn Glu Tyr Phe Ser Glu Ala Thr Asp Val Asp Ala Val
                405                 410                 415 gtc tat tta atg ttg gcc aat aat ctg att cac aag att ttc cca gac     1297
Val Tyr Leu Met Leu Ala Asn Asn Leu Ile His Lys Ile Phe Pro Asp
            420                 425                 430 gca act gtt att gcc gaa gat gtt tct ggt atg ccg ggc ctt agc cgg     1345
Ala Thr Val Ile Ala Glu Asp Val Ser Gly Met Pro Gly Leu Ser Arg
        435                 440                 445 cct gtt tct gag gga gga att ggt ttt gat tac cgc ctg gca atg gca     1393
Pro Val Ser Glu Gly Gly Ile Gly Phe Asp Tyr Arg Leu Ala Met Ala
    450                 455                 460 atc cca gat aag tgg ata gat tat tta aag aat aag aat gat gaa gat     1441
Ile Pro Asp Lys Trp Ile Asp Tyr Leu Lys Asn Lys Asn Asp Glu Asp
465                 470                 475                 480 tgg tcc atg aag gaa gta aca tcg agt ttg aca aat agg aga tat aca     1489
Trp Ser Met Lys Glu Val Thr Ser Ser Leu Thr Asn Arg Arg Tyr Thr
                485                 490                 495 gag aag tgt ata gca tat gcg gag agc cat gat cag tct att gtc ggt     1537
Glu Lys Cys Ile Ala Tyr Ala Glu Ser His Asp Gln Ser Ile Val Gly
            500                 505                 510 gac aag acc att gca ttt ctc cta atg aac aaa gag atg tat tct ggc     1585
Asp Lys Thr Ile Ala Phe Leu Leu Met Asn Lys Glu Met Tyr Ser Gly
        515                 520                 525 atg tct tgc ttg aca gat gct tct cct gtt gtt gat gca gga att gcg     1633
Met Ser Cys Leu Thr Asp Ala Ser Pro Val Val Asp Ala Gly Ile Ala
    530                 535                 540 ctt gac aag atg atc cat ttt ttt cac aat ggc ctt ggg agg aga ggg     1681
Leu Asp Lys Met Ile His Phe Phe His Asn Gly Leu Gly Arg Arg Gly
545                 550                 555                 560 gta cct caa ttt cat ggg taacgagttt ggccatcctg agtggattga            1729
Val Pro Gln Phe His Gly
                565 cttccctagt gagggcaata attggagtta tgacaaatgt agacgccagt ggaacctcgc   1789 agatagcgaa cacttgagat acaagtttat gaatgcattt gatagagcta tgaattcgct   1849 cgatgaaaag ttctcattcc tcgcatcagg aaaacagata gtaagcagca tggatgatga   1909 taataaggtt gttgtgtttg aacgtggtga cctggtattt gtattcaact ccacccaaa    1969 taacacatac gaagggtata agttggatg tgacttgcca gggaagtaca gagttgcact    2029 ggacagtgat gcttgggaat tggtggcca tggaagagct ggtcatgatg ttgaccattt    2089 cacatcacca gaaggaatac ctggagttcc agaaacaaat ttcaatggtc gtccaaattc   2149 cttcaaagtg ctgtctcctg cgcgaacatg tgtggcttat tacagagttg atgaacgcat   2209
```

-continued

```
gtcataaact gaagattacc agacagacat ttgtagtgag ctactaccaa cagccaatat    2269
cgaggaaagt gacgagaaac ttaaagattc atcatctaca aatatcagta catcatctac    2329
aaaaaatgct tattacagag ttgatgaacg catgtcagaa gctgaagatt accagacaga    2389
catttgtagt gagctactac taccaacagc caatatcgag gagagtgacg agaaacttga    2449
tgattcatta tctacaaata tcagtaacat tggtcagact gttgtagttt ctgttgagga    2509
gagagacaag gaacttaaag attcaccatc tgtaagcatc attagtgatg ctgttccagc    2569
tgaatgggct gattcggatg caaacgtctg gggtgaggac tagtcagatg attgatcgat    2629
ccttctacgt tggtgatctc ggtccgtgca tgatgtcttc agggtggtag cattgactga    2689
ttgcatcata gtttttttt tttttttaa gtatttcctc tatgcatatt attagcatcc    2749
aataaattta ctggttgttg tacatagaaa aagtgcattt gcatgtatgt gtttctctga    2809
aattttcccc agttttggtg ctttgccttt ggagccaagt ctctatatgt aataagaaaa    2869
ctaagaacaa tcacatatat aaaatgttag tagattacca                          2909
```

<210> SEQ ID NO 2
<211> LENGTH: 566
<212> TYPE: PRT
<213> ORGANISM: Solanum tuberosum

<400> SEQUENCE: 2

```
Gln Glu Arg Ser Trp Asp Ile Ser Ser Thr Pro Lys Ser Arg Val Arg
1               5                   10                  15

Lys Asp Glu Arg Met Lys His Ser Ser Ala Ile Ser Ala Val Leu Thr
            20                  25                  30

Asp Asp Asn Ser Thr Met Ala Pro Leu Glu Glu Asp Val Asn Thr Glu
        35                  40                  45

Asn Ile Gly Leu Leu Asn Leu Asp Pro Thr Leu Glu Pro Tyr Leu Asp
    50                  55                  60

His Phe Arg His Arg Met Lys Arg Tyr Val Asp Gln Lys Met Leu Ile
65                  70                  75                  80

Glu Lys Tyr Glu Gly Pro Leu Glu Glu Phe Ala Gln Gly Tyr Leu Lys
                85                  90                  95

Phe Gly Phe Asn Arg Glu Asp Gly Cys Ile Val Tyr Arg Glu Trp Ala
            100                 105                 110

Pro Ala Ala Gln Glu Ala Glu Val Ile Gly Asp Phe Asn Gly Arg Asn
        115                 120                 125

Gly Ser Asn His Met Met Glu Lys Asp Gln Phe Gly Val Trp Ser Ile
    130                 135                 140

Arg Ile Pro Asp Val Asp Ser Lys Pro Val Ile Pro His Asn Ser Arg
145                 150                 155                 160

Val Lys Phe Arg Phe Lys His Gly Asn Gly Val Trp Val Asp Arg Ile
                165                 170                 175

Pro Ala Trp Ile Lys Tyr Ala Thr Ala Asp Ala Thr Lys Phe Ala Ala
            180                 185                 190

Pro Tyr Asp Gly Val Tyr Trp Asp Pro Pro Ser Glu Arg Tyr His
        195                 200                 205

Phe Lys Tyr Pro Arg Pro Pro Lys Pro Ala Pro Arg Ile Tyr Glu
    210                 215                 220

Ala His Val Gly Met Ser Ser Glu Pro Arg Val Asn Ser Tyr Arg
225                 230                 235                 240

Glu Phe Ala Asp Asp Val Leu Pro Arg Ile Lys Ala Asn Asn Tyr Asn
                245                 250                 255
```

-continued

```
Thr Val Gln Leu Met Ala Ile Met Glu His Ser Tyr Tyr Gly Ser Phe
            260                 265                 270
Gly Tyr His Val Thr Asn Phe Phe Ala Val Ser Asn Arg Tyr Gly Asn
        275                 280                 285
Pro Glu Asp Leu Lys Tyr Leu Ile Asp Lys Ala His Ser Leu Gly Leu
    290                 295                 300
Gln Val Leu Val Asp Val Val His Ser His Ala Ser Asn Asn Val Thr
305                 310                 315                 320
Asp Gly Leu Asn Gly Phe Asp Ile Gly Gln Gly Ser Gln Glu Ser Tyr
                325                 330                 335
Phe His Ala Gly Glu Arg Gly Tyr His Lys Leu Trp Asp Ser Arg Leu
            340                 345                 350
Phe Asn Tyr Ala Asn Trp Glu Val Leu Arg Phe Leu Leu Ser Asn Leu
        355                 360                 365
Arg Trp Trp Leu Glu Glu Tyr Asn Phe Asp Gly Phe Arg Phe Asp Gly
    370                 375                 380
Ile Thr Ser Met Leu Tyr Val His His Gly Ile Asn Met Gly Phe Thr
385                 390                 395                 400
Gly Asn Tyr Asn Glu Tyr Phe Ser Glu Ala Thr Asp Val Asp Ala Val
                405                 410                 415
Val Tyr Leu Met Leu Ala Asn Asn Leu Ile His Lys Ile Phe Pro Asp
            420                 425                 430
Ala Thr Val Ile Ala Glu Asp Val Ser Gly Met Pro Gly Leu Ser Arg
        435                 440                 445
Pro Val Ser Glu Gly Gly Ile Gly Phe Asp Tyr Arg Leu Ala Met Ala
    450                 455                 460
Ile Pro Asp Lys Trp Ile Asp Tyr Leu Lys Asn Lys Asn Asp Glu Asp
465                 470                 475                 480
Trp Ser Met Lys Glu Val Thr Ser Ser Leu Thr Asn Arg Arg Tyr Thr
                485                 490                 495
Glu Lys Cys Ile Ala Tyr Ala Glu Ser His Asp Gln Ser Ile Val Gly
            500                 505                 510
Asp Lys Thr Ile Ala Phe Leu Leu Met Asn Lys Glu Met Tyr Ser Gly
        515                 520                 525
Met Ser Cys Leu Thr Asp Ala Ser Pro Val Val Asp Ala Gly Ile Ala
    530                 535                 540
Leu Asp Lys Met Ile His Phe His Asn Gly Leu Gly Arg Arg Gly
545                 550                 555                 560
Val Pro Gln Phe His Gly
                565

<210> SEQ ID NO 3
<211> LENGTH: 2853
<212> TYPE: DNA
<213> ORGANISM: Triticum aestivum
<220> FEATURE:
<221> NAME/KEY: CDS
<222> LOCATION: (313)..(2499)
<223> OTHER INFORMATION: BRANCHING ENZYME

<400> SEQUENCE: 3
gtgagatctg ggcgactggc tgactcaatc actacgcggg gatggcgacg tttcgcggtg     60
tccggcgcga ctctcggtgt ggcgcgggcc ggcgtcggag tggcgcgggc cggctcggag    120
cggaggggcg gggcggactt gccgtcgctg ctcctcagga agaaggactc ctctcgcgcc    180
```

-continued

```
gtcctgagcc gcgcggcctc tccagggaag gtcctggtgc ctgacggcga gagcgacgac      240
ttggcaagtc cggcgcaacc tgaagaatta cagatacctg aagatatcca ggagcaaacg      300
gcggaagtga ac atg aca ggg ggg act gca gaa aaa ctt caa tct tca gaa      351
              Met Thr Gly Gly Thr Ala Glu Lys Leu Gln Ser Ser Glu
              1               5                   10 ccg act cag ggc att gtg gaa aca atc act gat ggt gta acc aaa gga        399
Pro Thr Gln Gly Ile Val Glu Thr Ile Thr Asp Gly Val Thr Lys Gly
    15                  20                  25 gtt aag gaa cta gtc gtg ggg gag aaa ccg cga gtt gtc cca aaa cca        447
Val Lys Glu Leu Val Val Gly Glu Lys Pro Arg Val Val Pro Lys Pro
30              35                  40                  45 gga gat ggg cag aaa ata tac gag att gac cca aca ctg aaa gat ttt        495
Gly Asp Gly Gln Lys Ile Tyr Glu Ile Asp Pro Thr Leu Lys Asp Phe
                50                  55                  60 cgg agc cat ctt gac tac cga tac cgc gaa tac aag aga att cgt gct        543
Arg Ser His Leu Asp Tyr Arg Tyr Arg Glu Tyr Lys Arg Ile Arg Ala
            65                  70                  75 gct att gac caa cat gaa ggt gga ttg gaa gca ttt tct cgt ggt tat        591
Ala Ile Asp Gln His Glu Gly Gly Leu Glu Ala Phe Ser Arg Gly Tyr
        80                  85                  90 gaa aag ctt gga ttt acc cgc agt gct gaa ggt atc act tac cga gaa        639
Glu Lys Leu Gly Phe Thr Arg Ser Ala Glu Gly Ile Thr Tyr Arg Glu
    95                  100                 105 tgg gct cct gga gcg cat tct gca gca tta gta ggt gac ttc aac aat        687
Trp Ala Pro Gly Ala His Ser Ala Ala Leu Val Gly Asp Phe Asn Asn
110             115                 120                 125 tgg aat cca aat gca gat gct atg acc aga gat gat tat ggt gtt tgg        735
Trp Asn Pro Asn Ala Asp Ala Met Thr Arg Asp Asp Tyr Gly Val Trp
                130                 135                 140 gag att ttc ctc cct aac aac gct gat gga tcc tca gct att cct cat        783
Glu Ile Phe Leu Pro Asn Asn Ala Asp Gly Ser Ser Ala Ile Pro His
            145                 150                 155 ggc tca cgt gta aag ata cgg atg gat act cca tcc ggt gtg aag gat        831
Gly Ser Arg Val Lys Ile Arg Met Asp Thr Pro Ser Gly Val Lys Asp
        160                 165                 170 tca att tct gct tgg atc aag ttc tct gtg cag gct cca ggt gaa ata        879
Ser Ile Ser Ala Trp Ile Lys Phe Ser Val Gln Ala Pro Gly Glu Ile
    175                 180                 185 cct ttc aat ggc ata tat tat gat cca cct gaa gag gag aag tat gtc        927
Pro Phe Asn Gly Ile Tyr Tyr Asp Pro Pro Glu Glu Glu Lys Tyr Val
190             195                 200                 205 ttc caa cat cct caa cct aaa cga cca gag tca cta agg att tat gaa        975
Phe Gln His Pro Gln Pro Lys Arg Pro Glu Ser Leu Arg Ile Tyr Glu
                210                 215                 220 tca cac att gga atg agc agc ccg gaa ccg aag ata aat tca tat gct       1023
Ser His Ile Gly Met Ser Ser Pro Glu Pro Lys Ile Asn Ser Tyr Ala
            225                 230                 235 aat ttt agg gat gag gtg ttg cca aga att aaa agg ctt gga tac aat       1071
Asn Phe Arg Asp Glu Val Leu Pro Arg Ile Lys Arg Leu Gly Tyr Asn
        240                 245                 250 gca gtg cag ata atg gca atc cag gag cat tca tac tat gca agc ttt       1119
Ala Val Gln Ile Met Ala Ile Gln Glu His Ser Tyr Tyr Ala Ser Phe
    255                 260                 265 ggg tac cat gtt act aat ttt ttt gca cca agt agc cgt ttt gga act       1167
Gly Tyr His Val Thr Asn Phe Phe Ala Pro Ser Ser Arg Phe Gly Thr
270             275                 280                 285 cca gag gac tta aaa tcc ttg atc gat aga gca cat gag ctt ggt ttg       1215
Pro Glu Asp Leu Lys Ser Leu Ile Asp Arg Ala His Glu Leu Gly Leu
                290                 295                 300
```

-continued

| | |
|---|---|
| ctt gtt ctt atg gat att gtt cat agt cat tcg tca aat aat acc ctt<br>Leu Val Leu Met Asp Ile Val His Ser His Ser Ser Asn Asn Thr Leu<br>305 310 315 | 1263 |
| gac ggt ttg aat ggt ttc gat ggc act gat aca cat tac ttc cac ggt<br>Asp Gly Leu Asn Gly Phe Asp Gly Thr Asp Thr His Tyr Phe His Gly<br>320 325 330 | 1311 |
| ggt cca cgc ggc cat cat tgg atg tgg gat tct cgt cta ttc aac tat<br>Gly Pro Arg Gly His His Trp Met Trp Asp Ser Arg Leu Phe Asn Tyr<br>335 340 345 | 1359 |
| ggg agt tgg gaa gta ttg aga ttc tta ctg tca aac gcg aga tgg tgg<br>Gly Ser Trp Glu Val Leu Arg Phe Leu Leu Ser Asn Ala Arg Trp Trp<br>350 355 360 365 | 1407 |
| ctt gaa gaa tat aat ttt gat gga ttt cga ttt gat ggg gtg acc tcc<br>Leu Glu Glu Tyr Asn Phe Asp Gly Phe Arg Phe Asp Gly Val Thr Ser<br>370 375 380 | 1455 |
| atg atg tat act cac cat gga tta caa atg aca ttt act ggg aac tat<br>Met Met Tyr Thr His His Gly Leu Gln Met Thr Phe Thr Gly Asn Tyr<br>385 390 395 | 1503 |
| ggc gaa tat ttt gga ttt gct act gat gtt gat gcg gta gtt tac ttg<br>Gly Glu Tyr Phe Gly Phe Ala Thr Asp Val Asp Ala Val Val Tyr Leu<br>400 405 410 | 1551 |
| atg ctg gtc aac gat cta att cat gga ctt tat cct gat gct gta tcc<br>Met Leu Val Asn Asp Leu Ile His Gly Leu Tyr Pro Asp Ala Val Ser<br>415 420 425 | 1599 |
| att ggt gaa gat gtc agt gga atg cct aca ttt tgc atc cct gtt cca<br>Ile Gly Glu Asp Val Ser Gly Met Pro Thr Phe Cys Ile Pro Val Pro<br>430 435 440 445 | 1647 |
| gat ggt ggt gtt ggt ttt gac tac cgc ctg cat atg gct gta gca gat<br>Asp Gly Gly Val Gly Phe Asp Tyr Arg Leu His Met Ala Val Ala Asp<br>450 455 460 | 1695 |
| aaa tgg att gaa ctc ctc aag caa agt gac gaa tct tgg aaa atg ggc<br>Lys Trp Ile Glu Leu Leu Lys Gln Ser Asp Glu Ser Trp Lys Met Gly<br>465 470 475 | 1743 |
| gat att gtg cac acc cta aca aat aaa agg tgg ctt gag aag tgt gta<br>Asp Ile Val His Thr Leu Thr Asn Lys Arg Trp Leu Glu Lys Cys Val<br>480 485 490 | 1791 |
| act tat gca gaa agt cat gat caa gca cta gtt ggt gac aag act att<br>Thr Tyr Ala Glu Ser His Asp Gln Ala Leu Val Gly Asp Lys Thr Ile<br>495 500 505 | 1839 |
| gca ttc tgg ttg atg gat aag gat atg tat gat ttc atg gct ctg gat<br>Ala Phe Trp Leu Met Asp Lys Asp Met Tyr Asp Phe Met Ala Leu Asp<br>510 515 520 525 | 1887 |
| agg cct tca act cct cgc att gat cgt ggc ata gca tta cat aaa atg<br>Arg Pro Ser Thr Pro Arg Ile Asp Arg Gly Ile Ala Leu His Lys Met<br>530 535 540 | 1935 |
| atc agg ctt gtc acc atg ggt tta ggt ggt gaa agc tat ctt aac ttc<br>Ile Arg Leu Val Thr Met Gly Leu Gly Gly Glu Ser Tyr Leu Asn Phe<br>545 550 555 | 1983 |
| atg gga aat gag ttt ggg cat cct gaa tgg ata gat ttt cca aga ggc<br>Met Gly Asn Glu Phe Gly His Pro Glu Trp Ile Asp Phe Pro Arg Gly<br>560 565 570 | 2031 |
| cca caa act ctt cca acc ggc aaa gtt ctc cct gga aat aac aat aat<br>Pro Gln Thr Leu Pro Thr Gly Lys Val Leu Pro Gly Asn Asn Asn Asn<br>575 580 585 | 2079 |
| tat gat aaa tgc cgc cgt aga ttt gat ctt gga gat gca gaa ttt ctt<br>Tyr Asp Lys Cys Arg Arg Arg Phe Asp Leu Gly Asp Ala Glu Phe Leu<br>590 595 600 605 | 2127 |
| aga tat cgt ggt atg caa gag ttc gat cag gca atg cag cat ctt gag<br>Arg Tyr Arg Gly Met Gln Glu Phe Asp Gln Ala Met Gln His Leu Glu | 2175 |

-continued

```
                      610                 615                 620
gaa aaa tat ggg ttt atg aca tct gag cac cag tat gtt tca cgg aaa            2223
Glu Lys Tyr Gly Phe Met Thr Ser Glu His Gln Tyr Val Ser Arg Lys
                625                 630                 635 cat gag gaa gat aag gtg atc atc ttc gaa aga gga gat ttg gta ttt            2271
His Glu Glu Asp Lys Val Ile Ile Phe Glu Arg Gly Asp Leu Val Phe
            640                 645                 650 gtt ttc aac ttc cac tgg agc aat agc ttt ttt gac tac cgt gtt ggg            2319
Val Phe Asn Phe His Trp Ser Asn Ser Phe Phe Asp Tyr Arg Val Gly
        655                 660                 665 tgt tcc aag cct ggg aag tac aag gtg gcc ttg gac tcc gac gat gca            2367
Cys Ser Lys Pro Gly Lys Tyr Lys Val Ala Leu Asp Ser Asp Asp Ala
670                 675                 680                 685 ctc ttt ggt gga ttc agc agg ctt gat cat gat gtc gac tac ttc aca            2415
Leu Phe Gly Gly Phe Ser Arg Leu Asp His Asp Val Asp Tyr Phe Thr
                690                 695                 700 acc gaa cat ccg cat gac aac agg ccg cgc tct ttc tcg gtg tac act            2463
Thr Glu His Pro His Asp Asn Arg Pro Arg Ser Phe Ser Val Tyr Thr
            705                 710                 715 ccg agc aga act gcg gtc gtg tat gcc ctt aca gag taagaaccag                 2509
Pro Ser Arg Thr Ala Val Val Tyr Ala Leu Thr Glu
        720                 725 cagcggcttg ttacaaggca agagagaaac tccagagagc tcgtggatcg tgagcgaagc          2569
gacgggcaac ggcgcgaggc tgctccaagc gccatgactg ggagggatc gtgcctcttc           2629 cccagatgcc aggaggagca gatggatagg tagcttgttg gtgagcgctc gaaagaaaat          2689
ggacgggcct gggtgtttgt tgtgctgcac tgaaccctcc tcctatcttg cacattcccg          2749 gttgttttg tacatataac taataattgc ccgtgcgctt caacatgaac atataaatat           2809
tctaataggt tatcccgtga aaaaaaaaaa aaaaaaaaa aaaa                            2853
```

<210> SEQ ID NO 4
<211> LENGTH: 729
<212> TYPE: PRT
<213> ORGANISM: Triticum aestivum

<400> SEQUENCE: 4

```
Met Thr Gly Gly Thr Ala Glu Lys Leu Gln Ser Ser Glu Pro Thr Gln
1               5                   10                  15

Gly Ile Val Glu Thr Ile Thr Asp Gly Val Thr Lys Gly Val Lys Glu
            20                  25                  30

Leu Val Val Gly Glu Lys Pro Arg Val Pro Lys Pro Gly Asp Gly
        35                  40                  45

Gln Lys Ile Tyr Glu Ile Asp Pro Thr Leu Lys Asp Phe Arg Ser His
    50                  55                  60

Leu Asp Tyr Arg Tyr Arg Glu Tyr Lys Arg Ile Arg Ala Ala Ile Asp
65                  70                  75                  80

Gln His Glu Gly Gly Leu Glu Ala Phe Ser Arg Gly Tyr Glu Lys Leu
                85                  90                  95

Gly Phe Thr Arg Ser Ala Glu Gly Ile Thr Tyr Arg Glu Trp Ala Pro
            100                 105                 110

Gly Ala His Ser Ala Ala Leu Val Gly Asp Phe Asn Asn Trp Asn Pro
        115                 120                 125

Asn Ala Asp Ala Met Thr Arg Asp Asp Tyr Gly Val Trp Glu Ile Phe
    130                 135                 140

Leu Pro Asn Asn Ala Asp Gly Ser Ser Ala Ile Pro His Gly Ser Arg
145                 150                 155                 160
```

-continued

Val Lys Ile Arg Met Asp Thr Pro Ser Gly Val Lys Asp Ser Ile Ser
            165                 170                 175
Ala Trp Ile Lys Phe Ser Val Gln Ala Pro Gly Glu Ile Pro Phe Asn
            180                 185                 190
Gly Ile Tyr Tyr Asp Pro Pro Glu Glu Lys Tyr Val Phe Gln His
            195                 200                 205
Pro Gln Pro Lys Arg Pro Glu Ser Leu Arg Ile Tyr Glu Ser His Ile
            210                 215                 220
Gly Met Ser Ser Pro Glu Pro Lys Ile Asn Ser Tyr Ala Asn Phe Arg
225                 230                 235                 240
Asp Glu Val Leu Pro Arg Ile Lys Arg Leu Gly Tyr Asn Ala Val Gln
            245                 250                 255
Ile Met Ala Ile Gln Glu His Ser Tyr Tyr Ala Ser Phe Gly Tyr His
            260                 265                 270
Val Thr Asn Phe Phe Ala Pro Ser Ser Arg Phe Gly Thr Pro Glu Asp
            275                 280                 285
Leu Lys Ser Leu Ile Asp Arg Ala His Glu Leu Gly Leu Leu Val Leu
            290                 295                 300
Met Asp Ile Val His Ser His Ser Ser Asn Asn Thr Leu Asp Gly Leu
305                 310                 315                 320
Asn Gly Phe Asp Gly Thr Asp Thr His Tyr Phe His Gly Gly Pro Arg
            325                 330                 335
Gly His His Trp Met Trp Asp Ser Arg Leu Phe Asn Tyr Gly Ser Trp
            340                 345                 350
Glu Val Leu Arg Phe Leu Leu Ser Asn Ala Arg Trp Trp Leu Glu Glu
            355                 360                 365
Tyr Asn Phe Asp Gly Phe Arg Phe Asp Gly Val Thr Ser Met Met Tyr
            370                 375                 380
Thr His His Gly Leu Gln Met Thr Phe Thr Gly Asn Tyr Gly Glu Tyr
385                 390                 395                 400
Phe Gly Phe Ala Thr Asp Val Asp Ala Val Val Tyr Leu Met Leu Val
            405                 410                 415
Asn Asp Leu Ile His Gly Leu Tyr Pro Asp Ala Val Ser Ile Gly Glu
            420                 425                 430
Asp Val Ser Gly Met Pro Thr Phe Cys Ile Pro Val Pro Asp Gly Gly
            435                 440                 445
Val Gly Phe Asp Tyr Arg Leu His Met Ala Val Ala Asp Lys Trp Ile
            450                 455                 460
Glu Leu Leu Lys Gln Ser Asp Glu Ser Trp Lys Met Gly Asp Ile Val
465                 470                 475                 480
His Thr Leu Thr Asn Lys Arg Trp Leu Glu Lys Cys Val Thr Tyr Ala
            485                 490                 495
Glu Ser His Asp Gln Ala Leu Val Gly Asp Lys Thr Ile Ala Phe Trp
            500                 505                 510
Leu Met Asp Lys Asp Met Tyr Asp Phe Met Ala Leu Asp Arg Pro Ser
            515                 520                 525
Thr Pro Arg Ile Asp Arg Gly Ile Ala Leu His Lys Met Ile Arg Leu
            530                 535                 540
Val Thr Met Gly Leu Gly Gly Glu Ser Tyr Leu Asn Phe Met Gly Asn
545                 550                 555                 560
Glu Phe Gly His Pro Glu Trp Ile Asp Phe Pro Arg Gly Pro Gln Thr
            565                 570                 575

-continued

```
Leu Pro Thr Gly Lys Val Leu Pro Gly Asn Asn Asn Asn Tyr Asp Lys
            580             585                 590

Cys Arg Arg Arg Phe Asp Leu Gly Asp Ala Glu Phe Leu Arg Tyr Arg
        595             600             605

Gly Met Gln Glu Phe Asp Gln Ala Met Gln His Leu Glu Glu Lys Tyr
    610             615             620

Gly Phe Met Thr Ser Glu His Gln Tyr Val Ser Arg Lys His Glu Glu
625             630             635             640

Asp Lys Val Ile Ile Phe Glu Arg Gly Asp Leu Val Phe Val Phe Asn
            645             650             655

Phe His Trp Ser Asn Ser Phe Phe Asp Tyr Arg Val Gly Cys Ser Lys
            660             665             670

Pro Gly Lys Tyr Lys Val Ala Leu Asp Ser Asp Asp Ala Leu Phe Gly
        675             680             685

Gly Phe Ser Arg Leu Asp His Asp Val Asp Tyr Phe Thr Thr Glu His
    690             695             700

Pro His Asp Asn Arg Pro Arg Ser Phe Ser Val Tyr Thr Pro Ser Arg
705             710             715             720

Thr Ala Val Val Tyr Ala Leu Thr Glu
                725
```

NUCLEOTIDE SEQUENCES ENCODING ENZYMES THAT ALTER THE CARBOHYDRATE CONCENTRATION AND COMPOSITION IN PLANTS

RELATED APPLICATION

This application is a continuation of U.S. application Ser. No. 08/726,705, filed on Oct. 7, 1996, now abandoned, which was a continuation-in-part of U.S. application Ser. No. 08/104,158, filed on Aug. 13, 1993, now U.S. Pat. No. 6,215,042, based on International Application Serial No. PCT/EP92/00302, filed on Feb. 11, 1992, and German application Ser. No. P 41 04 782.6, filed on Feb. 13, 1991.

BACKGROUND OF THE INVENTION

1. Field of the Invention

The present invention relates to nucleotide sequences which encode enzymes involved in the formation of carbohydrates in plants and, more particularly to sequences which, after insertion into a plant genome, alter the carbohydrate concentration and composition in transformed plants and plant cells.

2. Description of the Related Art

Because of the continuous growth in the world population, there is a continuously growing demand for nutrients and raw materials. It is one of the goals of biotechnological research to achieve a modification in the content as well as in the yield of crops.

Of particular interest is the possibility of using plant ingredients as renewable sources of raw material sources, e.g. for the chemical industry. The use of plant ingredients as renewable sources of raw materials is of great importance for two reasons. First, mineral oil and coal deposits which are the main sources of raw materials for the petrochemical industry are finite. Therefore, alternative, renewable raw material sources must be developed.

Second, there is a surplus of crops grown for their nutritive properties in Europe and North America which has led to financial and political problems. The modification of plants to produce alternative products for which there is a higher quantitative demand could solve this problem.

Renewable raw materials can be divided into fats and oils, proteins and carbohydrates, such as mono-, di-, oligo- and polysaccharides. The most important polysaccharides are starch and cellulose. In the European Economic Community, the total starch production in 1987–1988 was obtained from maize (60%), wheat (19%) and potato (21%).

In order to increase the use of plant starch as an industrial raw material, the quantity of the starch must meet the demands of the processing industry. Important considerations include the ratio of amylose to amylopectin, the chain length of the starch, the branching grade of the amylopectin, and the size of the starch granules.

The main biochemical synthetic pathways for the production of starch in higher plants are well known. Starch consists of amylose and amylopectin. Amylose consists of a linear $\alpha$-1,3-glucan and amylopectin consists of $\alpha$-1,4-glucans, which are connected to each other by $\alpha$-1,6 linkages, and thus form a branched phytoglycogen. The so-called branching enzyme (Q-enzyme) is responsible for the introduction of the $\alpha$-1,6-linkage. One method for the production of starch which only has a linear $\alpha$-1,4-glucan structure is by the inhibition of the enzymatic activity of the proteins and/or the inhibition of the biosynthesis of the branching enzyme.

New biotechnology processes for the genetic alteration of dicotyledonous and monocotyledonous plants by transfer and stable installation of single isolated genes or groups of genes are known (Gasser and Fraley, Science 244, 1293–1299). The possibility of specific expression of foreign genes inserted in the plant by gene technology, primarily in potato tubers, is also known (EP 375092 and Rocha-Sosa et al., EMBO J. 8, 23–29 (1989)).

SUMMARY OF THE INVENTION

It is therefore an object of the present invention to provide nucleotide sequences which encode enzymes involved in the formation of carbohydrates in plants.

It is an additional object of the present invention to provide DNA sequences which can be used to alter the carbohydrate concentration and composition in transgenic cells and plants.

It is a further object of the present invention to provide plasmids, plant cells and plants containing the nucleotide sequences.

In the context of the invention, the term "plant" means a commercially useful plant, preferably maize, barley, wheat, rice, peas, soya beans, sugar cane, sugar beet, tomato, potato or tobacco. "Isolated" means having a higher purity than exists in nature, but does not require purification from a natural source. Isolated nucleotides encoding a branching enzyme may be produced synthetically, or by isolating cDNA thereof from a cDNA library or by any of the numerous other methods well understood in the art.

Other features and advantages of the present invention will become apparent from the following description of the invention which refers to the accompanying drawings.

BRIEF DESCRIPTION OF THE DRAWINGS

The patent file contains at least one drawing executed in color. Copies of this patent with color drawing(s) will be provided by the U.S. Patent and Trademark Office upon request and payment of the necessary fee.

A=Fragment A (529 bp) contains the 35s promoter of the cauliflower mosaic virus (CaMV). The fragment contains the nucleotides 6909–7437 of the cauliflower mosaic virus.

B=Fragment B (2909 bp) contains the DNA fragment which codes for the branching enzyme.

C=Fragment C (192 bp) contains the polyadenylation signal of gene 3 of the T-DNA of the Ti-plasmid pTiACH5 from nucleotide 11749 to 11939.

Also shown are the cleavage sites described in Example 1.

Figure 2:
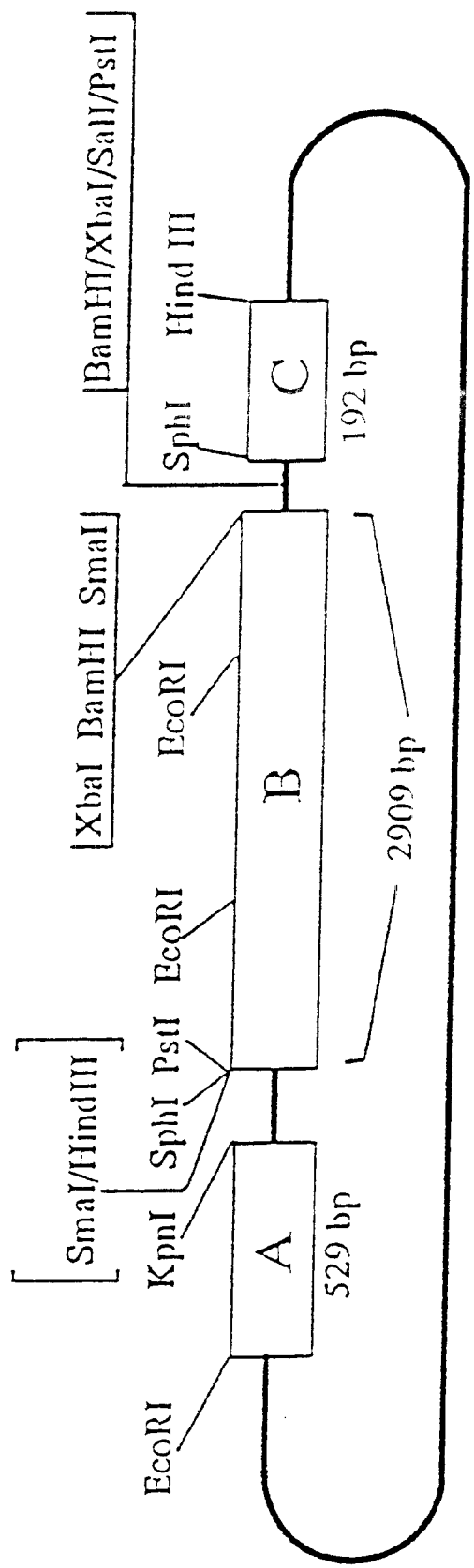

FIG. 2 shows the restriction map of the 13.6 kb plasmid P35s-anti-BE. The plasmid contains the following fragments:

A=Fragment A (529 bp) contains the 35s promoter of the cauliflower mosaic virus (CaMV). The fragment contains the nucleotides 6909 to 7437 of the CaMV.

B=Fragment B (2909 bp) contains the DNA, fragment which codes for the branching enzyme.

C=Fragment C (192 bp) contains the polyadenylation signal of gene 3 of the T-DNA of the Ti-plasmid pTiACH5. The fragment contains nucleotides 11749–11939.

Also shown are the cleavage sites described in Example 2.

Figure 3:
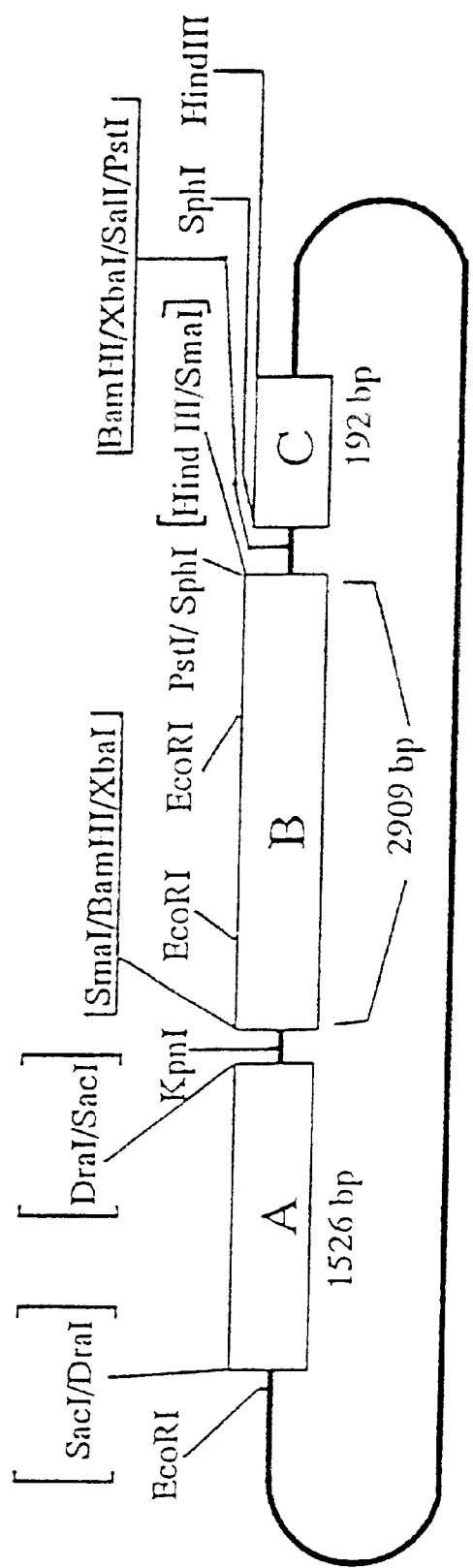

FIG. 3 shows the restriction map of the 14.6 kb plasmid P33-DE. The plasmid contains the following fragments.

A=Fragment A (1526 bp) contains the DraI-DraI-fragment of the promoter region of the patatin-gene B33. The fragment contains the nucleotide positions −1512 to +14.

B=Fragment B (2909 bp) contains the DNA fragment which codes for the branching enzyme.

C=Fragment C (192 bp) contains the polyadenylation signal of gene 3 of the T-DNA of the Ti-plasmid pTiACH5. The fragment contains nucleotides 11749–11939.

Also shown are the cleavage sites described in Example 3.

Figure 4:
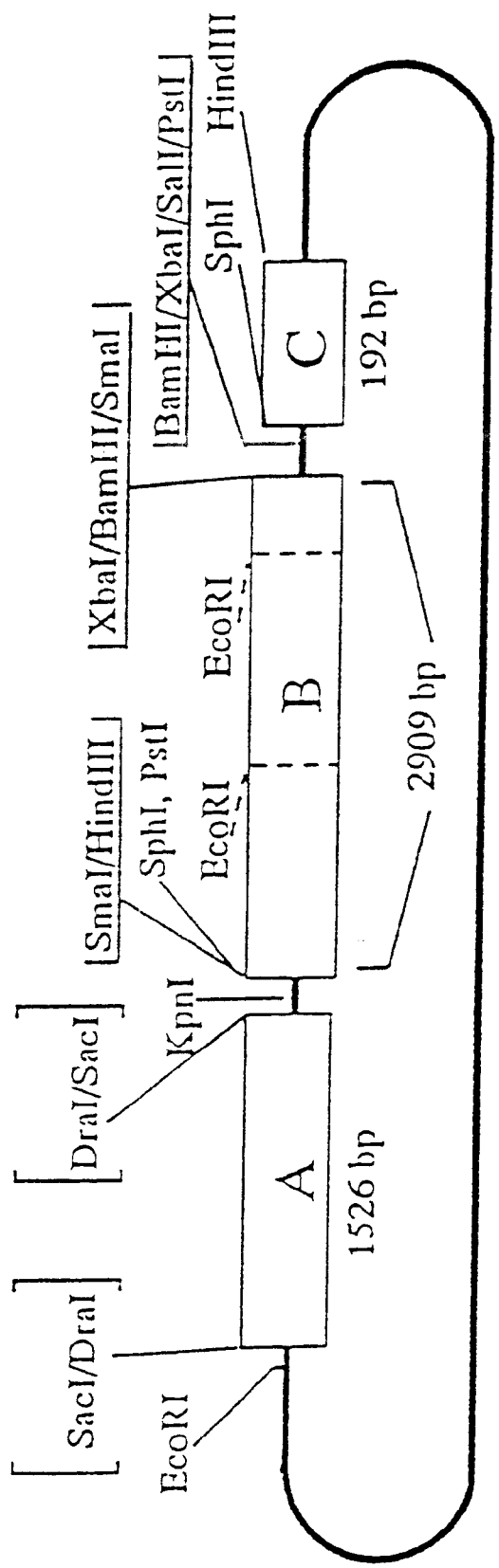

FIG. 4 shows the restriction map of the 14.6 plasmid P33-anti-BE. Plasmid contains the following fragments:

A=Fragment A (1526 bp) contains the DraI-DraI fragment of the promoter region of the patatin gene B 33. The fragment contains the nucleotide position −1512 to +14.

B=Fragment B (2909 bp) contains the cDNA-fragment which codes for the branching enzyme.

C=Fragment C (192 bp) contains the polyadenylation signal of the gene 3 of the T-DNA of the Ti-plasmid pTiACH5. The fragment contains the nucleotide positions 11749–11939.

Also shown are the cleavage sites described in Example 4.

Figure 5:
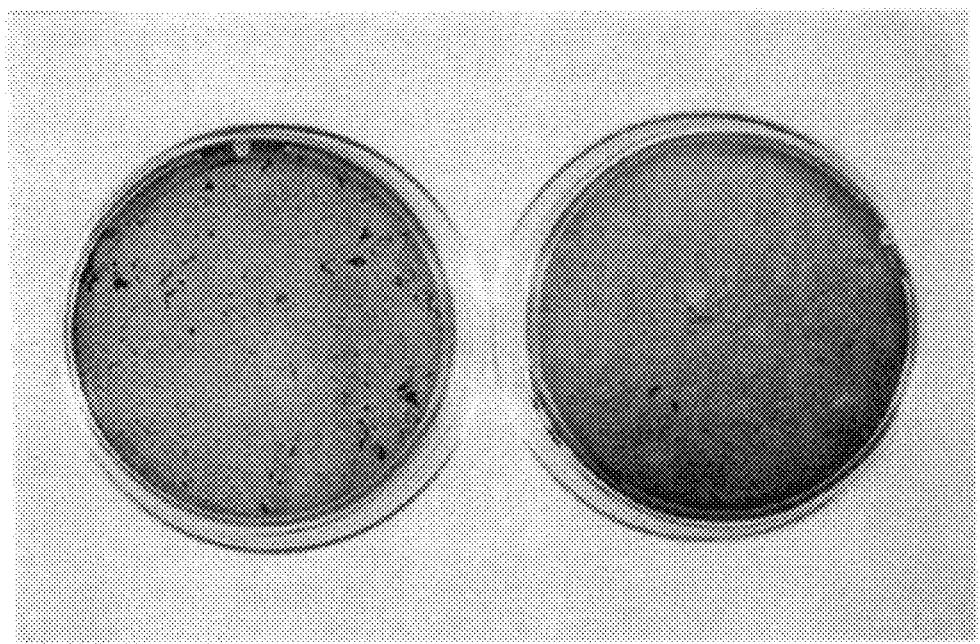

FIG. 5 shows two Petri dishes which identify the soluble components of tuber material from wildtype and modified plants. The right dish shows wildtype phytoglycogen (violet), while the left shows modified phytoglycogen (blue).

DETAILED DESCRIPTION OF THE INVENTION

Novel DNA sequences have been identified which encode enzymes involved in the formation of carbohydrates in plants. Plasmids which include these sequences can be used to transform plant cells to produce plant cells and plants which have an altered carbohydrate composition and concentration. In particular, DNA sequences derived from potato and wheat plants have been identified. The following DNA sequence (SEQ ID NO:1) encodes a branching enzyme isolated from a potato plant. The corresponding amino acid sequence is identified as SEQ ID NO:2.

```
T CAG GAG CGG TCT TGG GAT ATT TCT TCC ACC CCA AAA TCA AGA GTT         46
  Gln Glu Arg Ser Trp Asp Ile Ser Ser Thr Pro Lys Ser Arg Val
   1           5                  10                 15

AGA AAA GAT GAA AGG ATG AAG CAC AGT TCA GCT ATT TCC GCT GTT TTG       94
Arg Lys Asp Glu Arg Met Lys His Ser Ser Ala Ile Ser Ala Val Leu
                 20              25              30

ACC GAT GAC AAT TCG ACA ATG GCA CCC CTA GAG GAA GAT GTC AAC ACT      142
Thr Asp Asp Asn Ser Thr Met Ala Pro Leu Glu Glu Asp Val Asn Thr
             35              40              45

GAA AAT ATT GGC CTC CTA AAT TTG GAT CCA ACT TTG GAA CCT TAT CTA      190
Glu Asn Ile Gly Leu Leu Asn Leu Asp Pro Thr Leu Glu Pro Tyr Leu
         50              55              60

GAT CAC TTC AGA CAC AGA ATG AAG AGA TAT GTG GAT CAG AAA ATG CTC      238
Asp His Phe Arg His Arg Met Lys Arg Tyr Val Asp Gln Lys Met Leu
     65              70              75

ATT GAA AAA TAT GAG GGA CCC CTT GAG GAA TTT GCT CAA GGT TAT TTA      286
Ile Glu Lys Tyr Glu Gly Pro Leu Glu Glu Phe Ala Gln Gly Tyr Leu
 80              85              90              95

AAA TTT GGA TTC AAC AGG GAA GAT GGT TGC ATA GTC TAT CGT GAA TGG      334
Lys Phe Gly Phe Asn Arg Glu Asp Gly Cys Ile Val Tyr Arg Glu Trp
                100             105             110

GCT CCT GCT GCT CAG GAA GCA GAA GTT ATT GGC GAT TTC AAT GGT AGG      382
Ala Pro Ala Ala Gln Glu Ala Glu Val Ile Gly Asp Phe Asn Gly Arg
             115             120             125

AAC GGT TCT AAC CAC ATG ATG GAG AAG GAC CAG TTT GGT GTT TGG AGT      430
Asn Gly Ser Asn His Met Met Glu Lys Asp Gln Phe Gly Val Trp Ser
         130             135             140

ATT AGA ATT CCT GAT GTT GAC AGT AAG CCA GTC ATT CCA CAC AAC TCC      478
Ile Arg Ile Pro Asp Val Asp Ser Lys Pro Val Ile Pro His Asn Ser
     145             150             155

AGA GTT AAG TTT CGT TTC AAA CAT GGT AAT GGA GTG TGG GTA GAT CGT      526
Arg Val Lys Phe Arg Phe Lys His Gly Asn Gly Val Trp Val Asp Arg
160             165             170             175

ATC CCT GCT TGG ATA AAG TAT GCC ACT GCA GAC GCC ACA AAG TTT GCA      574
Ile Pro Ala Trp Ile Lys Tyr Ala Thr Ala Asp Ala Thr Lys Phe Ala
                180             185             190

GCA CCA TAT GAT GGT GTC TAC TGG GAC CCA CCA CCT TCA GAA AGG TAC      622
Ala Pro Tyr Asp Gly Val Tyr Trp Asp Pro Pro Pro Ser Glu Arg Tyr
```

-continued

```
                  195                      200                        205
CAC TTC AAA TAC CCT CGC CCT CCC AAA CCC CGA GCC CCA CGA ATC TAC      670
His Phe Lys Tyr Pro Arg Pro Pro Lys Pro Arg Ala Pro Arg Ile Tyr
            210                 215                 220

GAA GCA CAT GTC GGC ATG AGC AGC TCT GAG CCA CGT GTA AAT TCG TAT      718
Glu Ala His Val Gly Met Ser Ser Ser Glu Pro Arg Val Asn Ser Tyr
            225                 230                 235

CGT GAG TTT GCA GAT GAT GTT TTA CCT CGG ATT AAG GCA AAT AAC TAT      766
Arg Glu Phe Ala Asp Asp Val Leu Pro Arg Ile Lys Ala Asn Asn Tyr
240                 245                 250                 255

AAT ACT GTC CAG TTG ATG GCC ATA ATG GAA CAT TCT TAC TAT GGA TCA      814
Asn Thr Val Gln Leu Met Ala Ile Met Glu His Ser Tyr Tyr Gly Ser
                260                 265                 270

TTT GGA TAT CAT GTT ACA AAC TTT TTT GCT GTG AGC AAT AGA TAT GGA      862
Phe Gly Tyr His Val Thr Asn Phe Phe Ala Val Ser Asn Arg Tyr Gly
                275                 280                 285

AAC CCG GAG GAC CTA AAG TAT CTG ATA GAT AAA GCA CAT AGC TTG GGT      910
Asn Pro Glu Asp Leu Lys Tyr Leu Ile Asp Lys Ala His Ser Leu Gly
                290                 295                 300

TTA CAG GTT CTG GTG GAT GTA GTT CAC AGT CAT GCA AGC AAT AAT GTC      958
Leu Gln Val Leu Val Asp Val Val His Ser His Ala Ser Asn Asn Val
            305                 310                 315

ACT GAT GGC CTC AAT GGC TTT GAT ATT GGC CAA GGT TCT CAA GAA TCC     1006
Thr Asp Gly Leu Asn Gly Phe Asp Ile Gly Gln Gly Ser Gln Glu Ser
320                 325                 330                 335

TAC TTT CAT GCT GGA GAG CGA GGG TAC CAT AAG TTG TGG GAT AGC AGG     1054
Tyr Phe His Ala Gly Glu Arg Gly Tyr His Lys Leu Trp Asp Ser Arg
                340                 345                 350

CTG TTC AAC TAT GCC AAT TGG GAG GTT CTT CGT TTC CTT CTT TCC AAC     1102
Leu Phe Asn Tyr Ala Asn Trp Glu Val Leu Arg Phe Leu Leu Ser Asn
                355                 360                 365

TTG AGG TGG TGG CTA GAA GAG TAT AAC TTT GAC GGA TTT CGA TTT GAT     1150
Leu Arg Trp Trp Leu Glu Glu Tyr Asn Phe Asp Gly Phe Arg Phe Asp
            370                 375                 380

GGA ATA ACT TCT ATG CTG TAT GTT CAT CAT GGA ATC AAT ATG GGA TTT     1198
Gly Ile Thr Ser Met Leu Tyr Val His His Gly Ile Asn Met Gly Phe
385                 390                 395

ACA GGA AAC TAT AAT GAG TAT TTC AGC GAG GCT ACA GAT GTT GAT GCT     1246
Thr Gly Asn Tyr Asn Glu Tyr Phe Ser Glu Ala Thr Asp Val Asp Ala
400                 405                 410                 415

GTG GTC TAT TTA ATG TTG GCC AAT AAT CTG ATT CAC AAG ATT TTC CCA     1294
Val Val Tyr Leu Met Leu Ala Asn Asn Leu Ile His Lys Ile Phe Pro
                420                 425                 430

GAC GCA ACT GTT ATT GCC GAA GAT GTT TCT GGT ATG CCG GGC CTT AGC     1342
Asp Ala Thr Val Ile Ala Glu Asp Val Ser Gly Met Pro Gly Leu Ser
                435                 440                 445

CGG CCT GTT TCT GAG GGA GGA ATT GGT TTT GAT TAC CGC CTG GCA ATG     1390
Arg Pro Val Ser Glu Gly Gly Ile Gly Phe Asp Tyr Arg Leu Ala Met
            450                 455                 460

GCA ATC CCA GAT AAG TGG ATA GAT TAT TTA AAG AAT AAG AAT GAT GAA     1438
Ala Ile Pro Asp Lys Trp Ile Asp Tyr Leu Lys Asn Lys Asn Asp Glu
465                 470                 475

GAT TGG TCC ATG AAG GAA GTA ACA TCG AGT TTG ACA AAT AGG AGA TAT     1486
Asp Trp Ser Met Lys Glu Val Thr Ser Ser Leu Thr Asn Arg Arg Tyr
480                 485                 490                 495

ACA GAG AAG TGT ATA GCA TAT GCG GAG AGC CAT GAT CAG TCT ATT GTC     1534
Thr Glu Lys Cys Ile Ala Tyr Ala Glu Ser His Asp Gln Ser Ile Val
                500                 505                 510

GGT GAC AAG ACC ATT GCA TTT CTC CTA ATG AAC AAA GAG ATG TAT TCT     1582
Gly Asp Lys Thr Ile Ala Phe Leu Leu Met Asn Lys Glu Met Tyr Ser
```

-continued

```
                515               520                525
GGC ATG TCT TGC TTG ACA GAT GCT TCT CCT GTT GTT GAT GCA GGA ATT    1630
Gly Met Ser Cys Leu Thr Asp Ala Ser Pro Val Val Asp Ala Gly Ile
            530                 535             540

GCG CTT GAC AAG ATG ATC CAT TTT TTT CAC AAT GGC CTT GGG AGG AGA    1678
Ala Leu Asp Lys Met Ile His Phe Phe His Asn Gly Leu Gly Arg Arg
        545                 550                 555

GGG GTA CCT CAA TTT CAT GGG TAACGAGTTT GGCCATCCTG AGTGGATTGA       1729
Gly Val Pro Gln Phe His Gly
560                 565

CTTCCCTAGT GAGGGCAATA ATTGGAGTTA TGACAAATGT AGACGCCAGT GGAACCTCGC  1789

AGATAGCGAA CACTTGAGAT ACAAGTTTAT GAATGCATTT GATAGAGCTA TGAATTCGCT  1849

CGATGAAAAG TTCTCATTCC TCGCATCAGG AAAACAGATA GTAAGCAGCA TGGATGATGA  1909

TAATAAGGTT GTTGTGTTTG AACGTGGTGA CCTGGTATTT GTATTCAACT TCCACCCAAA  1969

TAACACATAC GAAGGGTATA AGTTGGATG TGACTTGCCA GGGAAGTACA GAGTTGCACT   2029

GGACAGTGAT GCTTGGGAAT TTGGTGGCCA TGGAAGAGCT GGTCATGATG TTGACCATTT  2089

CACATCACCA GAAGGAATAC CTGGAGTTCC AGAAACAAAT TTCAATGGTC GTCCAAATTC  2149

CTTCAAAGTG CTGTCTCCTG CGCGAACATG TGTGGCTTAT TACAGAGTTG ATGAACGCAT  2209

GTCATAAACT GAAGATTACC AGACAGACAT TTGTAGTGAG CTACTACCAA CAGCCAATAT  2269

CGAGGAAAGT GACGAGAAAC TTAAAGATTC ATCATCTACA AATATCAGTA CATCATCTAC  2329

AAAAAATGCT TATTACAGAG TTGATGAACG CATGTCAGAA GCTGAAGATT ACCAGACAGA  2389

CATTTGTAGT GAGCTACTAC TACCAACAGC CAATATCGAG GAGAGTGACG AGAAACTTGA  2449

TGATTCATTA TCTACAAATA TCAGTAACAT TGGTCAGACT GTTGTAGTTT CTGTTGAGGA  2509

GAGAGACAAG GAACTTAAAG ATTCACCATC TGTAAGCATC ATTAGTGATG CTGTTCCAGC  2569

TGAATGGGCT GATTCGGATG CAAACGTCTG GGGTGAGGAC TAGTCAGATG ATTGATCGAT  2629

CCTTCTACGT TGGTGATCTC GGTCCGTGCA TGATGTCTTC AGGGTGGTAG CATTGACTGA  2689

TTGCATCATA GTTTTTTTTT TTTTTTTTAA GTATTTCCTC TATGCATATT ATTAGCATCC  2749

AATAAATTTA CTGGTTGTTG TACATAGAAA AAGTGCATTT GCATGTATGT GTTTCTCTGA  2809

AATTTTCCCC AGTTTTGGTG CTTTGCCTTT GGAGCCAAGT CTCTATATGT AATAAGAAAA  2869

CTAAGAACAA TCACATATAT AAAATGTTAG TAGATTACCA                        2909
```

A cDNA encoding a branching enzyme was also isolated from wheat. The cDNA clone was identified as TaBE2 and was characterized and sequenced. The TaBE2 clone is 2853 base pairs (SEQ ID NO:3). The putative coding region begins at base 313 and ends at base 2499. The deduced amino acid sequence includes 729 amino acids (SEQ ID NO:4). The coding region was found to be unique from but homologous to branching enzymes from other species.

```
GTGAGATCTG GGCGACTGGC TGACTCAATC ACTACGCGGG GATGGCGACG TTTCGCGGTG    60

TCCGGCGCGA CTCTCGGTGT GGCGCGGGCC GGCGTCGGAG TGGCGCGGGC CGGCTCGGAG   120

CGGAGGGGCG GGCGGACTT GCCGTCGCTG CTCCTCAGGA AGAAGGACTC CTCTCGCGCC    180

GTCCTGAGCC GCGCGGCCTC TCCAGGGAAG GTCCTGGTGC CTGACGGCGA GAGCGACGAC   240

TTGGCAAGTC CGGCGCAACC TGAAGAATTA CAGATACCTG AAGTATCCA GGAGCAAACG    300

GCGGAAGTGA AC ATG ACA GGG GGG ACT GCA GAA AAA CTT CAA TCT TCA       348
              Met Thr Gly Gly Thr Ala Glu Lys Leu Gln Ser Ser
                1               5                   10

GAA CCG ACT CAG GGC ATT GTG GAA ACA ATC ACT GAT GGT GTA ACC AAA    396
            Glu Pro Thr Gln Gly Ile Val Glu Thr Ile Thr Asp Gly Val Thr Lys
                    15                  20                  25
```

-continued

```
GGA GTT AAG GAA CTA GTC GTG GGG GAG AAA CCG CGA GTT GTC CCA AAA      444
Gly Val Lys Glu Leu Val Val Gly Glu Lys Pro Arg Val Val Pro Lys
         30                  35                  40

CCA GGA GAT GGG CAG AAA ATA TAC GAG ATT GAC CCA ACA CTG AAA GAT      492
Pro Gly Asp Gly Gln Lys Ile Tyr Glu Ile Asp Pro Thr Leu Lys Asp
 45                  50                  55                  60

TTT CGG AGC CAT CTT GAC TAC CGA TAC CGC GAA TAC AAG AGA ATT CGT      540
Phe Arg Ser His Leu Asp Tyr Arg Tyr Arg Glu Tyr Lys Arg Ile Arg
                 65                  70                  75

GCT GCT ATT GAC CAA CAT GAA GGT GGA TTG GAA GCA TTT TCT CGT GGT      588
Ala Ala Ile Asp Gln His Glu Gly Gly Leu Glu Ala Phe Ser Arg Gly
             80                  85                  90

TAT GAA AAG CTT GGA TTT ACC CGC AGT GCT GAA GGT ATC ACT TAC CGA      636
Tyr Glu Lys Leu Gly Phe Thr Arg Ser Ala Glu Gly Ile Thr Tyr Arg
         95                  100                 105

GAA TGG GCT CCT GGA GCG CAT TCT GCA GCA TTA GTA GGT GAC TTC AAC      684
Glu Trp Ala Pro Gly Ala His Ser Ala Ala Leu Val Gly Asp Phe Asn
    110                 115                 120

AAT TGG AAT CCA AAT GCA GAT GCT ATG ACC AGA GAT GAT TAT GGT GTT      732
Asn Trp Asn Pro Asn Ala Asp Ala Met Thr Arg Asp Asp Tyr Gly Val
125                 130                 135                 140

TGG GAC ATT TTC CTC CCT AAC AAC GCT GAT GGA TCC TCA GCT ATT CCT      780
Trp Glu Ile Phe Leu Pro Asn Asn Ala Asp Gly Ser Ser Ala Ile Pro
                145                 150                 155

CAT GGC TCA CGT GTA AAG ATA CGG ATG GAT ACT CCA TCC GGT GTG AAG      828
His Gly Ser Arg Val Lys Ile Arg Met Asp Thr Pro Ser Gly Val Lys
            160                 165                 170

GAT TCA ATT TCT GCT TGG ATC AAG TTC TCT GTG CAG GCT CCA GGT GAA      876
Asp Ser Ile Ser Ala Trp Ile Lys Phe Ser Val Gln Ala Pro Gly Glu
        175                 180                 185

ATA CCT TTC AAT GGC ATA TAT TAT GAT CCA CCT GAA GAG GAG AAG TAT      924
Ile Pro Phe Asn Gly Ile Tyr Tyr Asp Pro Pro Glu Glu Glu Lys Tyr
    190                 195                 200

GTC TTC CAA CAT CCT CAA CCT AAA CGA CCA GAG TCA CTA AGG ATT TAT      972
Val Phe Gln His Pro Gln Pro Lys Arg Pro Glu Ser Leu Arg Ile Tyr
205                 210                 215                 220

GAA TCA CAC ATT GGA ATG AGC AGC CCG GAA CCG AAG ATA AAT TCA TAT     1020
Glu Ser His Ile Gly Met Ser Ser Pro Glu Pro Lys Ile Asn Ser Tyr
                225                 230                 235

GCT AAT TTT AGG GAT GAG GTG TTG CCA AGA ATT AAA AGG CTT GGA TAC     1068
Ala Asn Phe Arg Asp Glu Val Leu Pro Arg Ile Lys Arg Leu Gly Tyr
            240                 245                 250

AAT GCA GTG CAG ATA ATG GCA ATC CAG GAG CAT TCA TAC TAT GCA AGC     1116
Asn Ala Val Gln Ile Met Ala Ile Gln Glu His Ser Tyr Tyr Ala Ser
        255                 260                 265

TTT GGG TAC CAT GTT ACT AAT TTT TTT GCA CCA AGT AGC CGT TTT GGA     1164
Phe Gly Tyr His Val Thr Asn Phe Phe Ala Pro Ser Ser Arg Phe Gly
    270                 275                 280

ACT CCA GAG GAC TTA AAA TCC TTG ATC GAT AGA GCA CAT GAG CTT GGT     1212
Thr Pro Glu Asp Leu Lys Ser Leu Ile Asp Arg Ala His Glu Leu Gly
285                 290                 295                 300

TTG CTT GTT CTT ATG GAT ATT GTT CAT AGT CAT TCG TCA AAT AAT ACC     1260
Leu Leu Val Leu Met Asp Ile Val His Ser His Ser Ser Asn Asn Thr
                305                 310                 315

CTT GAC GGT TTG AAT GGT TTC GAT GGC ACT GAT ACA CAT TAC TTC CAC     1308
Leu Asp Gly Leu Asn Gly Phe Asp Gly Thr Asp Thr His Tyr Phe His
            320                 325                 330

GGT GGT CCA CGC GGC CAT CAT TGG ATG TGG GAT TCT CGT CTA TTC AAC     1356
Gly Gly Pro Arg Gly His His Trp Met Trp Asp Ser Arg Leu Phe Asn
        335                 340                 345
```

-continued

```
TAT GGG AGT TGG GAA GTA TTG AGA TTC TTA CTG TCA AAC GCG AGA TGG         1404
Tyr Gly Ser Trp Glu Val Leu Arg Phe Leu Leu Ser Asn Ala Arg Trp
    350                 355                 360

TGG CTT GAA GAA TAT AAT TTT GAT GGA TTT CGA TTT GAT GGG GTG ACC         1452
Trp Leu Glu Glu Tyr Asn Phe Asp Gly Phe Arg Phe Asp Gly Val Thr
365                 370                 375                 380

TCC ATG ATG TAT ACT CAC CAT GGA TTA CAA ATG ACA TTT ACT GGG AAC         1500
Ser Met Met Tyr Thr His His Gly Leu Gln Met Thr Phe Thr Gly Asn
                385                 390                 395

TAT GGC GAA TAT TTT GGA TTT GCT ACT GAT GTT GAT GCG GTA GTT TAC         1548
Tyr Gly Glu Tyr Phe Gly Phe Ala Thr Asp Val Asp Ala Val Val Tyr
            400                 405                 410

TTG ATG CTG GTC AAC GAT CTA ATT CAT GGA CTT TAT CCT GAT GCT GTA         1596
Leu Met Leu Val Asn Asp Leu Ile His Gly Leu Tyr Pro Asp Ala Val
        415                 420                 425

TCC ATT GGT GAA GAT GTC AGT GGA ATG CCT ACA TTT TGC ATC CCT GTT         1644
Ser Ile Gly Glu Asp Val Ser Gly Met Pro Thr Phe Cys Ile Pro Val
    430                 435                 440

CCA GAT GGT GGT GTT GGT TTT GAC TAC CGC CTG CAT ATG GCT GTA GCA         1692
Pro Asp Gly Gly Val Gly Phe Asp Tyr Arg Leu His Met Ala Val Ala
445                 450                 455                 460

GAT AAA TGG ATT GAA CTC CTC AAG CAA AGT GAC GAA TCT TGG AAA ATG         1740
Asp Lys Trp Ile Glu Leu Leu Lys Gln Ser Asp Glu Ser Trp Lys Met
                465                 470                 475

GGC GAT ATT GTG CAC ACC CTA ACA AAT AAA AGG TGG CTT GAG AAG TGT         1788
Gly Asp Ile Val His Thr Leu Thr Asn Lys Arg Trp Leu Glu Lys Cys
            480                 485                 490

GTA ACT TAT GCA GAA AGT CAT GAT CAA GCA CTA GTT GGT GAC AAG ACT         1836
Val Thr Tyr Ala Glu Ser His Asp Gln Ala Leu Val Gly Asp Lys Thr
        495                 500                 505

ATT GCA TTC TGG TTG ATG GAT AAG GAT ATG TAT GAT TTC ATG GCT CTG         1884
Ile Ala Phe Trp Leu Met Asp Lys Asp Met Tyr Asp Phe Met Ala Leu
    510                 515                 520

GAT AGG CCT TCA ACT CCT CGC ATT GAT CGT GGC ATA GCA TTA CAT AAA         1932
Asp Arg Pro Ser Thr Pro Arg Ile Asp Arg Gly Ile Ala Leu His Lys
525                 530                 535                 540

ATG ATC AGG CTT GTC ACC ATG GGT TTA GGT GGT GAA AGC TAT CTT AAC         1980
Met Ile Arg Leu Val Thr Met Gly Leu Gly Gly Glu Ser Tyr Leu Asn
                545                 550                 555

TTC ATG GGA AAT GAG TTT GGG CAT CCT GAA TGG ATA GAT TTT CCA AGA         2028
Phe Met Gly Asn Glu Phe Gly His Pro Glu Trp Ile Asp Phe Pro Arg
            560                 565                 570

GGC CCA CAA ACT CTT CCA ACC GGC AAA GTT CTC CCT GGA AAT AAC AAT         2076
Gly Pro Gln Thr Leu Pro Thr Gly Lys Val Leu Pro Gly Asn Asn Asn
        575                 580                 585

AAT TAT GAT AAA TGC CGC CGT AGA TTT GAT CTT GGA GAT GCA GAA TTT         2124
Asn Tyr Asp Lys Cys Arg Arg Arg Phe Asp Leu Gly Asp Ala Glu Phe
    590                 595                 600

CTT AGA TAT CGT GGT ATG CAA GAG TTC GAT CAG GCA ATG CAG CAT CTT         2172
Leu Arg Tyr Arg Gly Met Gln Glu Phe Asp Gln Ala Met Gln His Leu
605                 610                 615                 620

GAG GAA AAA TAT GGG TTT ATG ACA TCT GAG CAC CAG TAT GTT TCA CGG         2220
Glu Glu Lys Tyr Gly Phe Met Thr Ser Glu His Gln Tyr Val Ser Arg
                625                 630                 635

AAA CAT GAG GAA GAT AAG GTG ATC ATC TTC GAA AGA GGA GAT TTG GTA         2268
Lys His Glu Glu Asp Lys Val Ile Ile Phe Glu Arg Gly Asp Leu Val
            640                 645                 650

TTT GTT TTC AAC TTC CAC TGG AGC AAT AGC TTT TTT GAC TAC CGT GTT         2316
Phe Val Phe Asn Phe His Trp Ser Asn Ser Phe Phe Asp Tyr Arg Val
        655                 660                 665
```

-continued

```
GGG TGT TCC AAG CCT GGG AAG TAC AAG GTG GCC TTG GAC TCC GAC GAT      2364
Gly Cys Ser Lys Pro Gly Lys Tyr Lys Val Ala Leu Asp Ser Asp Asp
    670                 675                 680

GCA CTC TTT GGT GGA TTC AGC AGG CTT GAT CAT GAT GTC GAC TAC TTC      2412
Ala Leu Phe Gly Gly Phe Ser Arg Leu Asp His Asp Val Asp Tyr Phe
685                 690                 695                 700

ACA ACC GAA CAT CCG CAT GAC AAC AGG CCG CGC TCT TTC TCG GTG TAC      2460
Thr Thr Glu His Pro His Asp Asn Arg Pro Arg Ser Phe Ser Val Tyr
                705                 710                 715

ACT CCG AGC AGA ACT GCG GTC GTG TAT GCC CTT ACA GAG TAAGAACCAG       2509
Thr Pro Ser Arg Thr Ala Val Val Tyr Ala Leu Thr Glu
            720                 725

CAGCGGCTTG TTACAAGGCA AAGAGAGAAC TCCAGAGAGC TCGTGGATCG TGAGCGAAGC    2569

GACGGGCAAC GGCGCGAGGC TGCTCCAAGC GCCATGACTG GGAGGGGATC GTGCCTCTTC    2629

CCCAGATGCC AGGAGGAGCA GATGGATAGG TAGCTTGTTG GTGAGCGCTC GAAAGAAAAT    2689

GGACGGGCCT GGGTGTTTGT TGTGCTGCAC TGAACCCTCC TCCTATCTTG CACATTCCCG    2749

GTTGTTTTTG TACATATAAC TAATAATTGC CCGTGCGCTT CAACATGAAC ATATAAATAT    2809

TCTAATAGGT TATCCCGTGA AAAAAAAAAA AAAAAAAAAA AAAA                     2853
```

Plasmids which contain the sequences of the invention can be used to modify the carbohydrate concentration and composition in plants. Carbohydrates which can be altered by the DNA sequences are mono-, di-, oligo- or polysaccharides. Starch is an example of a polysaccharide which can be modified in plants and plant cells. The sequences of the present invention encode branching enzymes which are involved in the formation of α-1,6-linkages in the production of starch. By blocking or increasing the formation of the α-1,6-linkage, the ratio of amylose to amylopectin can be altered in the starch of plant cells and plants.

The property of the branching enzyme to modify the amylose/amylopectin ratio in starch is not limited to coding sequences exactly as set forth herein. It is contemplated that the enzyme can be represented by slightly different nucleotide sequences. The property of the branching enzyme is also not changed when the plasmids containing the branching enzyme are modified in the plant cell or the plant.

The DNA sequences can be fused to the regulatory sequences of other genes for transcription of the DNA (coding) sequence of the branching enzyme. The DNA sequence can also be fused in an inverted direction to the regulatory sequences of other genes, whereby the 3'-end of the coding sequence is fused to the 3'-end of the promoter and the 5'-end of the coding sequence is fused to the 5'-end of the termination signal. In this way, an anti-sense RNA of the branching enzyme is produced in the plant. The regulatory sequences herein are promoters and termination signals of plant or viral genes, such as, for example, the promoter of 35s RNA of the cauliflower mosaic virus or the promoter of the class I patatin-gene B33 and the termination signal of the 3'-end of the octopine synthase gene of the T-DNA of the Ti-plasmid pTiACH5. However, as is well understood in the art, other sequences can be used.

The sequences of the present invention can be incorporated into plasmids for expression of the enzyme or for transformation into a plant cell.

Plant cells containing sequences can be regenerated in known manner to create transgenic plants. It is possible to simultaneously insert more than one copy of the sequences into a plant cell or plant.

The following plasmids were deposited at the Deutsche Sammlung von Mikroorganismen (DSM) in Braunschweig, Germany on Aug. 20, 1990 (deposit number):

| Plasmid | P35s-BE | (DSM 6143) |
| Plasmid | P35s-anti-BE | (DSM 6144) |
| Plasmid | P33-BE | (DSM 6145) |
| Plasmid | P3-anti-BE | (DSM 6146) |

The following general methods and Examples 1–6 are based on the sequence isolated from a potato plant (SEQ ID NO:1).

General Methods

1. Cloning Process

The vectors pU18/19 and pU118, and the M13mp 10 series (Yanisch-Perron et. al., Gene (1985), 33, 103–119) were used for cloning.

For plant transformation, the gene constructions were cloned into the binary vector BIN19 (Bevan, Nucl. Acids Res. (1984), 12, 8711–8720).

2. Bacterial Strains

The E. coli strain DMH71-18 (Messing et al., Proc. Natl. Acad. Sci. USA (1977), 24, 6342–6346) or TB1 was used for the pUC and M13M0 vectors.

For the vector BIN19, the E. coli. strain TB1 was used exclusively. TB1 is a recombinant-negative, tetracycline-resistant derivative of strain JM101 (Yanisch-Perron et al., Gene (1985), 33, 103–119). The genotype of the TB1 strain is F'(traD36, proAB, lacI, lacZAM15), Δ(lac, pro), SupE, LhiS, recA, Sr1::Tn10 (TcR) (Bart Barrel, personal communication).

The transformation of the plasmids into the potato plants was performed using the Agrobacterium tumefaciens strain LBA4404 (Bevan, M., Nucl. Acids Res. 12, 8711–8721, (1984); BIN19 derivative).

3. Transformation of Agrobacterium tumefaciens

In the case of BIN19 derivatives, the DNA was inserted into Agrobacteria by direct transformation in accordance with the method developed by Holsters et al., (Mol. Gen.

Genet. (1978), 163, 181–187). The plasmid DNA or transformed Agrobacteria was isolated in accordance with the method developed by Birnholm and Doly (Nucl. Acids Res. ((1979), 7, 1513–1533) and was separated by gel electrophoresis after suitable restriction cleavage.

4. Plant Transformation 10 small leaves, wounded with a scalpel, of a sterile potato culture were placed in 10 ml of MS medium with 2% sucrose containing from 30 to 50 μl of an *Agrobacterium tumefaciens* overnight culture grown under selection. After 3 to 5 minutes of gentle shaking, the Petri dishes were incubated in the dark at 25° C. After 2 days, the leaves were placed on MS medium with 1.6% glucose, 2 mg/l of zeatin ribose, 0.02 mg/l of, naphthylacetic acid, 0.02 mg/l of gibberellic acid, 500 mg/l of claforan, 50 mg/l of kanamycin and 0.8% Bacto agar. After incubation for one week at 25° C. and 3000 lux, the claforan concentration in the medium was reduced by half. The regeneration and cultivation of the plants were carried out according to known methods (Rocha-Sosa et al., EMBO Journal 8, 23–29 (1989).

5. Analysis of Genomic DNA from Transgenic Potato Plants

The isolation of genomic plant DNA was performed in accordance with Rogers and Bendich (Plant Mol. Biol. (1985), 5, 69–76.

For the DNA analysis, after suitable restriction cleavage, 10 to 20 μg of DNA were analyzed by means of Southern blots for the integration of the DNA sequences to be investigated.

6. Analysis of the Total RNA from Transgenic Potato Plants

The isolation of plant total RNA was carried out in accordance with Logemann et al. (Analytical Biochem. (1987), 163, 16–20.

Northern blots were used to analyze 50 μg portions of total RNA for the presence of the desired transcripts.

7. Protein Extraction

For the extraction of total protein from plant tissue, pieces of tissue were homogenized in protein extraction buffer (25 mM sodium phosphate pH 7.0, 2 mM sodium hydrogen sulphite), with the addition of 0.1% (w/v) of insoluble polyvinylpyrrolidone (PVP).

After filtration through cellulose, cell detritus was centrifuged off for 20 minutes at 10,000 revolutions per minute and the protein concentration of the supernatant was determined in accordance with the method developed by Bradford (Anal. Biochem. (1976)/72, 248–254).

8. Detection of Foreign Proteins by Means of Immunological Processes (Western Blot)

The protein extracts were separated according to molecular weight by means of gel electrophoresis in SDS-PAGE (sodium dodecyl sulphate polyacrylamide) gels. After SDS-PAGE, the protein gels were equilibrated for 15 to 30 minutes in transfer buffer for graphite electrodes (48 g/l of tris, 39 g/l of glycine, 0.0375% SDS, 20% methanol) and then transferred in a cooling chamber to a nitrocellulose filter and separated at 1.3 mA/cm$^2$ for from 1 to 2 hours. The filter was saturated for 30 minutes with 3% gelatin in TBS buffer (20 mM tris/HCl pH 7.5, 500 mM NaCl), and the filter was then incubated for 2 hours with the appropriate antiserum in a suitable dilution (1:1000–10000 in TBS buffer) at room temperature. The filter was then washed for 15 minutes each with TBS, TTBS (TBS buffer with 0.1% polyoxyethylene-(20)-sorbitan monolaurate) and TBS buffer. After being washed, the filter was incubated for 1 hour at room temperature with alkaline phosphatase-conjugated goat-anti-rabbit (GAR) antibodies (1:7500 in TBS). The filter was then washed as described above and equilibrated in AP buffer (100 mM tris/HCl pH 9.5, 100 mM NaCl, 5 mM MgCl$_2$). The alkaline phosphatase reaction was started by means of the substrate addition of 70 μl of 4-nitrotetrazolium (NBT) solution (50 mg/ml of NBT in 70% dimethyl-formamide) and 35 μl of 5-bromo-4-chloro-3-indolyl phosphate (BCIP) (50 mg/ml BCIP in dimethylformamide) in 50 ml of AP buffer. The first signals were observed after 2 minutes.

9. Determination of the Amylose/Amylopectin Ratio in Starch of Transgenic Potato Plants Leaf pieces having a diameter of 20 mm were floated in 6% sucrose solution under continuous light for 14 hours. This light incubation induced a strong increased starch formation in the leaf pieces. After incubation, the amylose and amylopectin concentration was determined according to Hovenkamp Hermelink et al. (Potato Research 31, 241–246 (1988)).

The following examples illustrate the preparation of the plasmids according to the invention, the insertion of sequences from those plasmids into the plant cell, as well as regeneration of transgenic plants, and the analysis of those transgenic plants.

EXAMPLES

Example 1

Preparation of the Plasmid P35s-BE and Insertion of the Plasmid into the Plant Genome of the Potato From a cDNA library in the expression vector λqt11, different clones were identified that cross-react with an antibody that is directed against the branching enzyme of potatoes. These clones were used to identify complete clones from a cDNA library in the HindIII position the vector pUC19 that originate from isolated mRNA of growing potato tubers. One clone isolated in this manner had an insert size of 2909 bp (SEQ ID NO:1). The 2909 bp long cDNA contained in this clone was used in the following examples and is identified therein as cBE.

For the preparation of a plasmid p35s-BE, the cDNA was linked to the promoter of the 35s-RNA of the cauliflower mosaic virus as well as to the polyadenylation signal of the octopine synthase gene of the Ti-plasmid pTiACH5. The cDNA coding for the branching enzyme was oriented so that the coding strain was readable (sense-orientation). The plasmid p35s-BE has a size of 13.6 kb and comprises the three fragments, A, B and C, which were cloned into the cleavage sites of the polylinker of BIN19.

Fragment A (529 bp) contains the 35s promoter of the cauliflower mosaic virus (CaMV). The fragment contains nucleotides 6909 to 7437 of the CaMV (Franck et al., Cell 21, 285–294). It was isolated as the EcoRI-KpnI-fragment from the plasmid pDH51 (Pietrzak et al. Nucleic Acids Research 14, 5057–5868) and was cloned between the EcoRI-KpnI-cleavage position of the polylinker of the plasmid BIN19.

Fragment B contains a 2909 bp cDNA fragment cBE which codes for the branching enzyme. It was cut out as HindIII-SmaI-fragment of the vector pUC19 and was cloned into the SmaI-position of the polylinker of BIN19 after filling in the HindIII-position with DNA polymerase. The cDNA was oriented so that the coding strand is readable and a sense-RNA is formed. The cleavage sites BamHI/XbaI and PstI/SphI originate from the polylinker of pUC19. The cleavage sites BamHI/XbaI/SalI/PstI originate from the polylinker of BIN19. The two EcoRI cleavage sites located on the fragment B are internal cleavage sites of the fragment.

Figure 1:
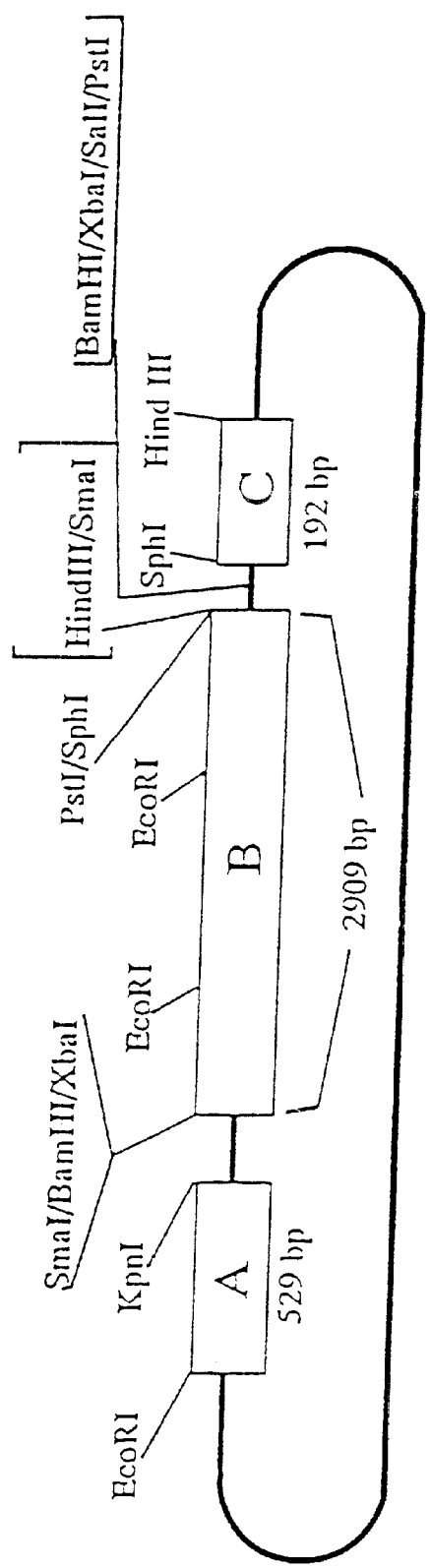
FIG. 1 shows the restriction map of the 13.6 kb plasmid P35s-BE. The plasmid contains the following fragments.

Fragment C (192 bp) contains the polyadenylation signal of gene 3 of the T-DNA of the Ti-plasmid PtiACH5 (Gielen et al., EMBO J. 3, 835–846). The fragment includes nucleotides 11749–11939, which were isolated as PvuII-HindIII fragment from the plasmid pAGV40 (Herrera-Estrella et al., (1983), Nature 303, 209–213) and were then cloned onto the PvuII cleavage site between the SphI-HindIII cleavage site of the polylinker of BIN19, after addition of SphI linkers (see FIG. 1).

The plasmid p35s-BE was transferred into potatoes using the agrobacterial system. After transformation, whole plants were regenerated. Protein extracts which were isolated from tubers of the transgenic plants were tested for the existence of the branching enzyme using western blot analysis. Further, tubers of these plants were tested for the content of amylose and amylopectin.

Example 2

Preparation of the Plasmid P35s-anti-BE and Introduction of the Plasmid the Plant Genome of Potato.

In a similar manner to that described in Example 1, the plasmid p35s-anti-BE was prepared. However, the orientation of the designated cDNA of the branching enzyme was inverted relative to the 35s promoter. The plasmid p35s-anti-BE has a size of 13.6 kb and comprises the three fragments, A, B and C, which were cloned in the cleavage sites of the polylinker of BIN19.

Fragment A (529 bp) contains the 35s promoter of the cauliflower mosaic virus (CaMV). The fragment contains the nucleotides 6909 to 7437 of the CaMV (Franck et al., Cell 21, 285–294), and was isolated as an EcoRI-KpnI-fragment from the plasmid pDH51 (Pietrzak et al., Nucleic Acids Research 14, 5857–5868) and cloned between the EcoRI-KpnI-cleavage site of the polylinker of the plasmid BIN19.

Fragment B contains the 2909 bp cDNA fragment cBE which codes for the branching enzyme. It was cut from the HindIII-SmaI-fragment of the vector pUC19 and cloned in the SmaI-position of the polylinker BIN19 after filling in the HindIII-position with DNA polymerase. The cDNA is oriented so that the non-coding strand is readable and an anti-sense-RNA is formed. The cleavage sites SphI, PstI and XbaI, BamHI, SmaI originate from the polylinker pUC19. The cutting positions BamHI/XbaI/SalI/PstI originate from the polylinker of BIN19. The two EcoRI cleavage sites contained on the fragment B are internal cleavage sites of this fragment.

Fragment C (192 bp) contains the polyadenylation signal of gene 3 of the T-DNA of the Ti-plasmid pTiACH5 (Gielen et al., EMBO J 3, 835–846). The fragment includes nucleotides 11749–11939, which were isolated as a PvuII-HindIII-fragment from the plasmid pAGV40 (Herrera-Estrella et-al. (1983), and which were cloned between the SphI-HindIII-cleavage position of the polylinker of BIN19 after addition of SphI-linkers to the PvuII cleavage position (see FIG. 2).

The plasmid p35s-anti-BE was transferred into potatoes using the agrobacterial system. After transformation, whole plants were regenerated.

Protein extracts, which had been isolated from tubers of these plants, were tested for the existence of the branching enzyme using western blot analysis. Tubers of the transformed plants were also tested for the content of amylose and amylopectin.

Example 3

Preparation of the Plasmid p33-BE and Introduction of the Plasmid into the Plant Genome of the Potato.

Plasmid p33-BE was prepared in accordance with the procedure described in Example 1, except that the 35s promoter was replaced with the promoter of the class I patatin-gene B33 (Rocha-Sosa et al. EMBO J, 8:23–29). The plasmid p33-BE has a size of 14.6 kb and consists of the three fragments, A, B and C, that were cloned into the cleavage position of the polylinker of BIN19.

Fragment A contains the DraI-DraI-fragment (position −1512 to position +14) of the promoter region of the patatin-gene B33 (Rocha-Sosa et al., EMBO J, 8 23–29), which had been cloned into the SacI-position of the polylinker of pUC18. For this, the overhanging 3'-end of the SacI-cleavage site had been rendered blunt by T4-DNA polymerase. After this, the EcoRI-BamHI-fragment was inserted between the EcoRI-BamHI-position of the polylinker of BIN19.

Fragment B contains the 2909 bp cDNA fragment cBE which codes for the branching enzyme. It was cut out as a HindIII-SmaI-fragment from the vector pUC19 and was cloned into the SmaI-position of the polylinker of BIN19 after the HindIII position was filled in with DNA polymerase. The cDNA was oriented so that the coding strand was readable and a sense-RNA was formed. The cleavage sites BamHI/XbaI and PstI/SphI originated from the polylinker of pUC19. The cutting positions BamHI/XbaI/SalI/PstI originated from the polylinker of BIN19. The two EcoRI-cleavage sites contained on the fragment B are internal cleavage sites of this fragment.

Fragment C (192 bp) contains the polyadenylation signal of gene 3 of the T-DNA of the Ti-plasmid PtiACH5 (Gielen et al., EMBO J 3, 835–846). The fragment includes nucleotides 11749–11939, which were isolated as PvuII-HindIII-fragment from the plasmid pAGV40 (Herrera-Estrella et al. (1983) Nature 303, 209–213) and which was cloned between the SphI-HindIII-cleavage site of the polylinker of BIN19 after addition of SphI-linkers to the PvuII-cleavage site.

The plasmid p33-BE was transferred into *Agrobacterium tumefaciens* and used for the transformation of potato plants.

Example 4

Preparation of the Plasmid p33-Anti-BE and Introduction of Plasmid into the Plant Genome of Potato Plasmid p33-anti-BE was prepared as described in Example 2, except that the 35s-promoter was replaced with the promoter of the class I patatin-gene B33 (Rocha-Sosa et al., EMBO J 8, 23–29). The plasmid p33-anti-BE has a size of 14.6 kb and consists of three fragments, A, B, and C, which were cloned into the cleavage sites of the polylinker of BIN19.

Fragment A contains the DraI-DraI-fragment (position −1512 to position +14) of the promoter region of the patatin-gene B33 (Rocha-Sosa et al., EMBO J 8, 23–29) which was first cloned into the SacI-position of the polylinker of pUC18. The overhanging 3'-ends of the SacI-cleavage site were rendered blunt by T4-DNA polymerase. After this the fragment was inserted as EcoRI-BamHI-fragment between the EcoRI-BamHI-position of the polylinker of BIN19.

Fragment B contains the 2909 bp cDNA fragment cBE which codes for the branching enzyme. It was cut out as HindIII-SmaI-fragment from the vector pUC18 and after filling in the HindIII-position with DNA polymerase, the fragment was cloned into the SmaI-position of the polylinker of BIN19. The cDNA was oriented so that the non-coding strand was readable and anti-sense-RNA could be formed. The cutting positions SphI, PstI and XbaI, BamHI, SmaI originate from the polylinker of pUC19. The cutting positions BamHI/XbaI/SalI/PstI originate from the polylinker of pUC19. The two EcoRI cleavage sites which are located on the fragment B are internal cleavage sites of the fragment.

Fragment C (192 bp) contains the polyadenylation signal of gene 3 of the T-DNA of the Ti-plasmid pTiACH5 (Gielen et al., EMBO J, 3 835–846). The fragment includes nucleotides 11749–11939, which had been isolated as PvuII-HindIII-fragment from the plasmid pAGV40 (Herrera-Estrella et al., (1983), Nature 303, 209–213) and which was cloned between the SphI-HindIII-cleavage site of the polylinker of BIN19 after addition of SphI-linkers to the PvuII cleavage sites.

The plasmid p33-anti-BE was introduced in *Agrobacterium tumefaciens* and was used for the transformation of potato plants.

Example 5

Nucleotides 166–2909 of the 2909 bp cDNA sequence described in Example 1, which code for the branching enzyme in the HindIII-cleavage site of the cloning vector pUC19, were inserted into the corresponding cleavage sites of the polylinker of the cloning vector pUC18. This allows the N-end of the α-peptide of the β-galactosidase located on the vector to be fused with a part of the branching enzyme. The functionality of the resulting fusion protein was tested in a mutant *Escherichia coli* (KV 832) which is deficient in the branching enzyme (Kiel et. al., Gene 78, 9–17). Cells transformed with this construct were plated out on YT-agar plates containing 0.5% glucose. The resulting colonies were stained with Lugolscher solution. The transformed plant cells showed a yellow-red color in contrast to the blue colored untransformed plant cells which indicates the branching activity of the fusion protein (Kiel et al Gene 78, 9–17). An overproduction of this protein in *Escherichia coli* enables the use as technical enzyme.

Example 6

Iodine Staining of Soluble Components of Tuber Material

Generally, starch is present in the plant cell as a water insoluble compound. However, starch can be solubilized in part, for example, by heating. The following procedure describes a qualitative determination of unbranched and branched phytoglycogens that are water soluble under the experimental procedure.

Potato tuber material was ground in a mortar and suspended in 50 mM Tris/HCl (pH 7.5). The suspension was mixed with an equal volume of 2% Agarose in hot water. The mixture was then poured into Petri dishes and, after hardening, stained with LUGOL's solution for 30 minutes. The result of a typical analysis of transgenic plants transformed by plasmids p35S-anti-BE or p33-anti-BE, respectively, is shown in FIG. 5. As shown in FIG. 5, the wildtype phytoglycogens stain violet due to the presence of blue staining amylose and red staining branched polyglucans. In contrast, in the tuber extracts from transgenic plants, only the blue staining of amylose can be seen.

Example 7

Construction of Plant Transformation Vectors with the cDNA Isolated from Wheat

The cDNA clone isolated from wheat (*Triticum aestivum L.*, cv Florida) (SEQ ID NO:3) was used to construct vectors based on the plasmid pUC19 to express two partial antisense RNAs of the isolated cDNA clone TaBE2 (SEQ ID NO:3). In both transformation vectors, a partial cDNA insert (size 2.5 kb and 1.1 kb) of plasmid pTaBE2 is attached to the multiple cloning site in antisense orientation. Expression is regulated by the ubiquitin promoter. This promoter consists of the first untranslated exon and the first intron of the ubiguitin1 gene from maize (Christensen A H, et al., Plant Molecular Biology, 18:675–689 (1992)).

Parts of the polylinker and the NOS-terminator were obtained from plasmid pact1.cas (CAMBIA, TG 0063, Cambia, GPO Box 3200, Cancerra ACT 2601, Australia). Vector constructs consisting of this terminator and constructs based on pact1.cas are described in McElroy et al. (Molecular Breeding, 1:27–37 (1995)).

The vectors pTaBE225-as and pTaBE211-as were used to transform wheat.

Although the present invention has been described in relation to particular embodiments thereof, many other variations and modifications and other uses will become apparent to those skilled in the art.

What is claimed is:

1. An isolated nucleic acid molecule comprising SEQ ID NO:3 or a molecule encoding a wheat branching enzyme comprising SEQ ID NO:4 and a molecule complementary thereto.

2. A procaryotic cell comprising the nucleic acid molecule according to claim 1.

3. The procaryotic cell according to claim 2, which is Agrobacterium.

4. A plant cell or plant transformed with the nucleic acid molecule according to claim 1.

5. The plant cell or plant according to claim 4, wherein the expression of branching enzyme is increased relative to a non-transformed plant cell or plant.

6. The plant cell or plant according to claim 4, wherein the expression of branching enzyme is reduced relative to a non-transformed plant cell or plant.

7. A method for producing a transformed plant cell, in which the number of alpha-1,6-linkages of glucose monomers in starch is altered relative to a non-transformed plant, comprising the step of introducing into a plant cell the nucleic acid molecule according to claim 1.

8. A transformed plant cell obtained by the method according to claim 7.

9. The plant cell according to claim 8, selected from the group consisting of, maize, barley, wheat, rice, pea, soya bean, sugar beet, tomato, potato, and tobacco.

10. A method for producing a transformed plant, in which the number of alpha-1,6-linkages of glucose monomers in starch is altered relative to a non-transformed plant, comprising the step of introducing into a plant cell the nucleic acid molecule according to claim 1; and regenerating a plant from said plant cell.

11. A transformed plant obtained by the method according to claim 10.

12. The plant according to claim 11, selected from the group consisting of, maize, barley, wheat, rice, pea, soya bean, sugar beet, tomato, potato, and tobacco.

13. A recombinant expression vector comprising:
a) a promoter sequence; and
b) the nucleic acid molecule as specified in claim 1; and wherein said nucleic acid molecule is operably linked to said promoter sequence.

14. The recombinant expression vector according to claim 13, wherein said nucleic acid molecule is linked to said promoter sequence in sense orientation.

15. The recombinant expression vector according to claim 13, wherein said nucleic acid molecule is linked to said promoter sequence in antisense orientation.

16. A procaryotic cell comprising the recombinant expression vector according to claim 13.

17. The procaryotic cell according to claim 16, which is Agrobacterium.

18. A plant cell or plant transformed with the recombinant expression vector according to claim 13.

19. The plant cell or plant according to claim 18, wherein the expression of branching enzyme is increased relative to a non-transformed plant cell or plant.

20. The plant cell or plant according to claim 18, wherein the expression of branching enzyme is reduced relative to a non-transformed plant cell or plant.

21. A method for producing a transformed plant cell, in which the number of alpha-1,6-linkages of glucose monomers in starch is altered relative to a non-transformed plant, comprising the step of introducing into a plant cell the recombinant expression vector according to claim 13.

22. A transformed plant cell obtained by the method according to claim 21.

23. The plant cell according to claim 22, selected from the group consisting of, maize, barley, wheat, rice, pea, soya bean, sugar beet, tomato, potato, or tobacco.

24. A method for producing a transformed plant, in which the number of alpha-1,6-linkages of glucose monomers in starch is altered relative to a non-transformed plant, comprising the step of introducing into a plant cell the recombinant expressing vector according to claim 13; and regenerating a plant from said plant cell.

25. A transformed plant obtained by the method according to claim 24.

26. The plant according to claim 25, selected from the group consisting of, maize, barley, wheat, rice, pea, soya bean, sugar beet, tomato, potato, or tobacco.

* * * * *